US012642311B2

(12) United States Patent
Sakai

(10) Patent No.: US 12,642,311 B2
(45) Date of Patent: Jun. 2, 2026

(54) ELASTIC MEMBER AND DISPOSABLE WEARING ARTICLE INCLUDING ELASTIC MEMBER

(71) Applicant: Daio Paper Corporation, Ehime (JP)

(72) Inventor: Syunsuke Sakai, Tochigi (JP)

(73) Assignee: Daio Paper Corporation, Ehime (JP)

( * ) Notice: Subject to any disclaimer, the term of this patent is extended or adjusted under 35 U.S.C. 154(b) by 1304 days.

(21) Appl. No.: 16/636,863

(22) PCT Filed: Sep. 25, 2018

(86) PCT No.: PCT/JP2018/035309
§ 371 (c)(1),
(2) Date: Feb. 5, 2020

(87) PCT Pub. No.: WO2019/065572
PCT Pub. Date: Apr. 4, 2019

(65) Prior Publication Data
US 2020/0214362 A1 Jul. 9, 2020

(30) Foreign Application Priority Data

Sep. 27, 2017 (JP) ................................ 2017-187179
Nov. 24, 2017 (JP) ................................ 2017-226329

(51) Int. Cl.
*A41B 9/00* (2006.01)
*A41B 17/00* (2006.01)
(Continued)

(52) U.S. Cl.
CPC .............. *A41B 9/001* (2013.01); *A41B 9/004* (2013.01); *A41B 17/00* (2013.01);
(Continued)

(58) Field of Classification Search
CPC ......... A41B 9/001; A41B 9/004; A41B 17/00; A41B 2300/22; A41B 2400/52;
(Continued)

(56) References Cited

U.S. PATENT DOCUMENTS

2013/0158494 A1* 6/2013 Ong ........................ A61F 13/53
604/367
2018/0008481 A1 1/2018 Takahashi et al.
(Continued)

FOREIGN PATENT DOCUMENTS

JP 2014-198179 10/2014
JP 2015-204982 11/2015
(Continued)

OTHER PUBLICATIONS

International Search Report for PCT/JP2018/035309, mailed Nov. 6, 2018.

*Primary Examiner* — Kai H Weng
*Assistant Examiner* — Katherine-Ph Minh Pham
(74) *Attorney, Agent, or Firm* — Andrus Intellectual Property Law, LLP

(57) ABSTRACT
In an elastic member, a first sheet layer and a second sheet layer are formed of a material having translucency. An elastic sheet can be visually recognized through the first sheet layer and the second sheet layer. First non-joint bands linearly continuous along a first direction intersecting an stretchable direction at an acute angle are repeatedly present at intervals in a direction orthogonal to the first direction as non-joint bands in which a portion not having sheet joined portions is continuous in an unfolded state in a stretchable region. Sheet joined portions and joint holes are provided at intervals between adjacent first non-joint bands in the stretchable region. A unit structure including a plurality of first non-joint bands having different first widths determined as widths in the direction orthogonal to the first direction is
(Continued)

repeatedly present in the direction orthogonal to the first direction in the stretchable region.

11 Claims, 21 Drawing Sheets

(51) Int. Cl.

| | | |
|---|---|---|
| A61F 13/49 | (2006.01) |
| A61F 13/496 | (2006.01) |
| B29C 65/00 | (2006.01) |
| B29C 65/08 | (2006.01) |
| B29L 31/48 | (2006.01) |
| B32B 5/02 | (2006.01) |
| B32B 7/12 | (2006.01) |
| B32B 27/12 | (2006.01) |
| B32B 27/32 | (2006.01) |

(52) U.S. Cl.
CPC ...... *A61F 13/4902* (2013.01); *A61F 13/4963* (2013.01); *B29C 65/086* (2013.01); *B29C 66/21* (2013.01); *B29C 66/344* (2013.01); *B29C 66/7294* (2013.01); *B32B 5/022* (2013.01); *B32B 7/12* (2013.01); *B32B 27/12* (2013.01); *B32B 27/32* (2013.01); *A41B 2300/22* (2013.01); *A41B 2400/52* (2013.01); *A41B 2500/30* (2013.01); *A41B 2500/52* (2013.01); *A61F 2013/49022* (2013.01); *B29L 2031/4878* (2013.01); *B32B 2274/00* (2013.01); *B32B 2555/02* (2013.01)

(58) Field of Classification Search
CPC ............. A41B 2500/30; A41B 2500/52; A61F 13/4902; A61F 13/4963; A61F 2013/49022; A61F 13/49; A61F 13/496; A61F 13/51; A61F 13/49009; A61F 13/15585; A61F 13/15699; A61F 13/49014; A61F 13/515; A61F 2013/15861; A61F 2013/15886; B29C 65/086; B29C 66/21; B29C 66/344; B29C 66/7294; B29C 66/83415; B29C 66/41; B29C 66/433; B29C 66/81433; B29C 66/83511; B29C 66/1122; B29C 66/81429; B32B 5/022; B32B 7/12; B32B 27/12; B32B 27/32; B32B 2274/00; B32B 2555/02; B29L 2031/4878

See application file for complete search history.

(56) References Cited

U.S. PATENT DOCUMENTS

| | | | |
|---|---|---|---|
| 2018/0028371 A1 | 2/2018 | Takaishi | |
| 2018/0147094 A1* | 5/2018 | Takeuchi | .......... B29C 66/83511 |
| 2019/0117469 A1 | 4/2019 | Kunihiro | |

FOREIGN PATENT DOCUMENTS

| | | |
|---|---|---|
| JP | 2016-043247 | 4/2016 |
| JP | 5918877 | 5/2016 |
| JP | 5980355 | 8/2016 |
| JP | 5980367 | 8/2016 |
| JP | 2016-187385 | 11/2016 |
| JP | 2016-189932 | 11/2016 |
| JP | 2016-189933 | 11/2016 |
| JP | 6049228 | 12/2016 |
| JP | 2017-064226 | 4/2017 |
| JP | 2017-093732 | 6/2017 |
| JP | 2017-196296 | 11/2017 |
| WO | 2016-121976 | 8/2016 |
| WO | 2016-121980 | 8/2016 |

* cited by examiner

[FIG.1]
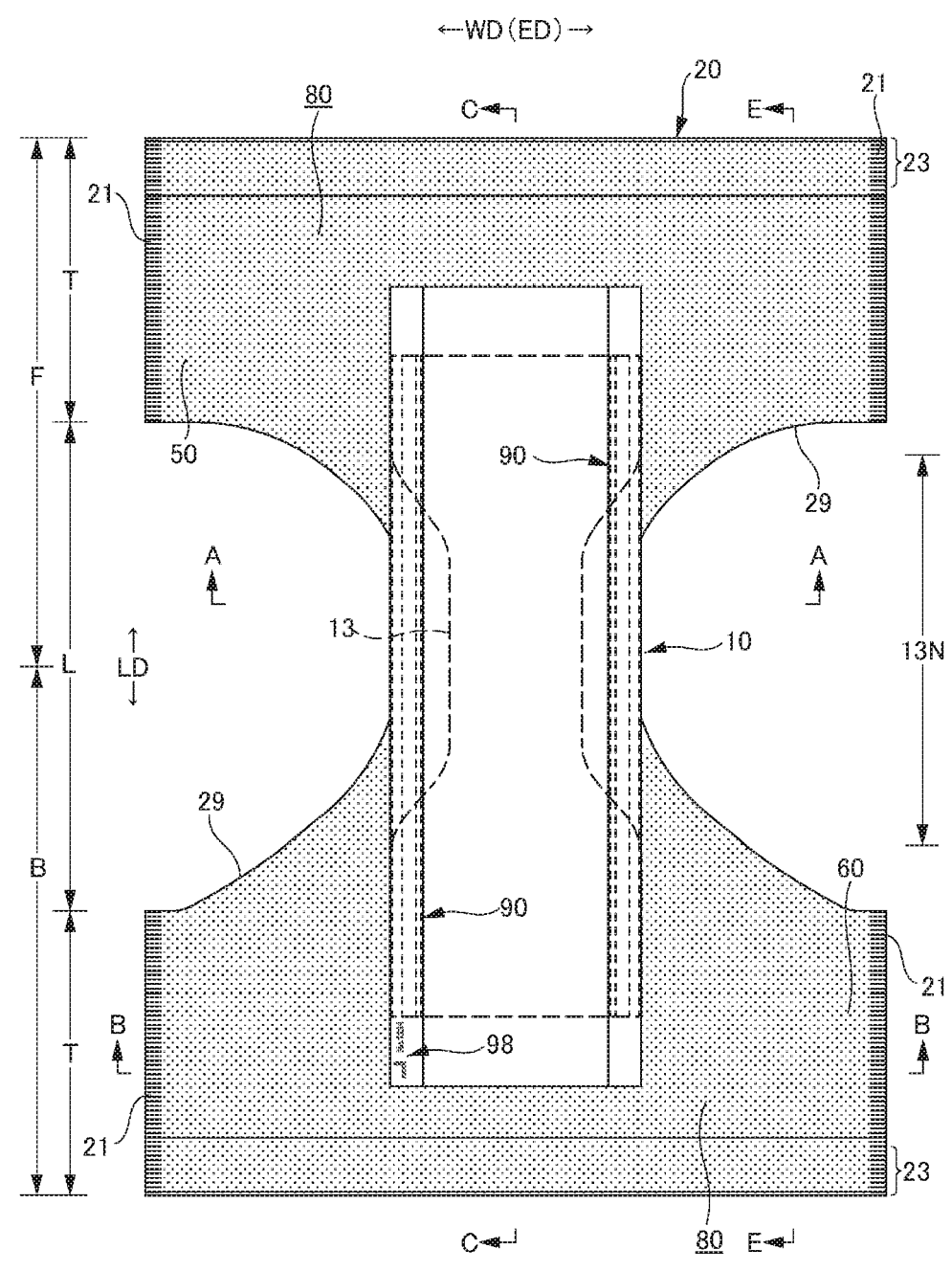

[FIG.2]
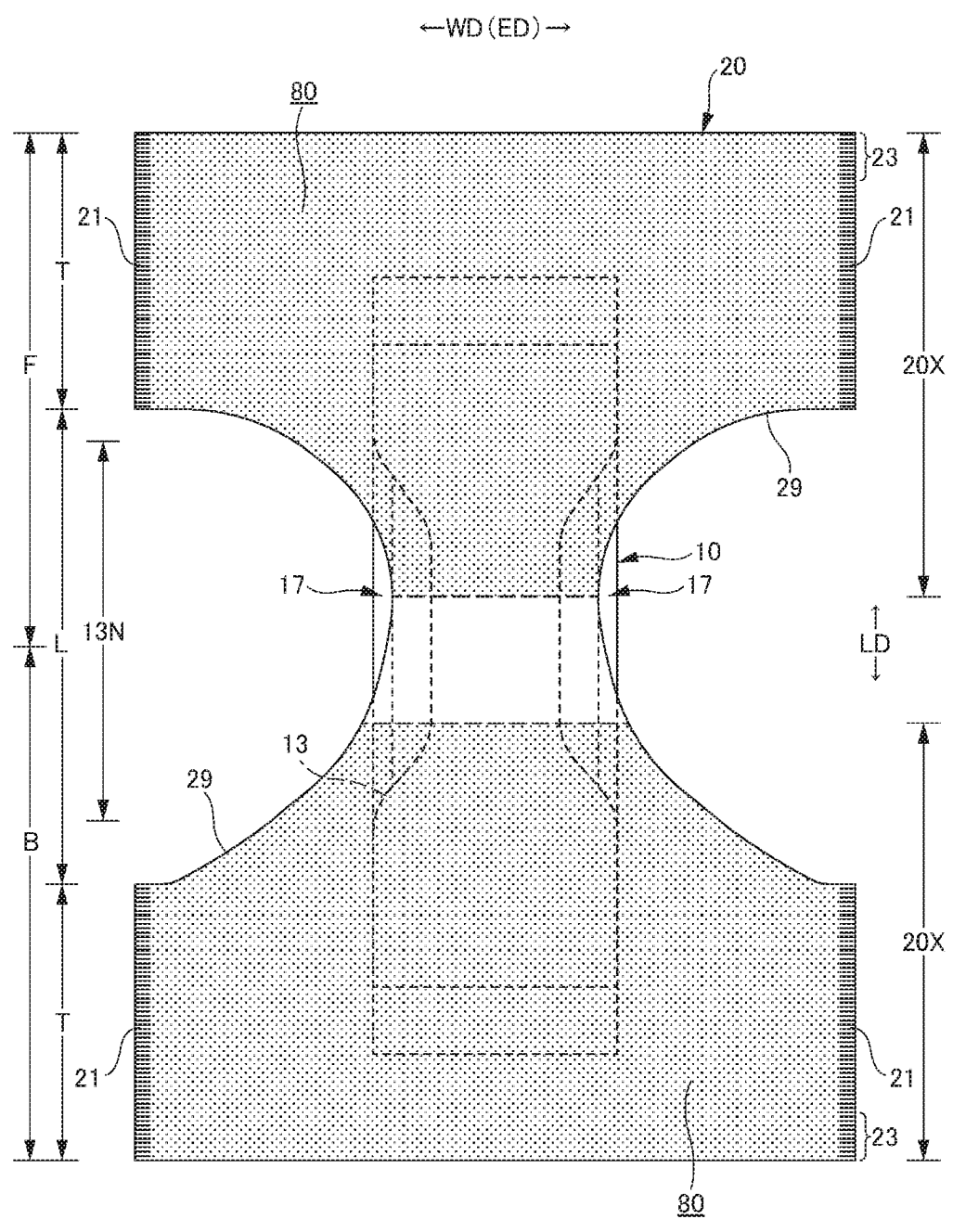

[FIG.3]
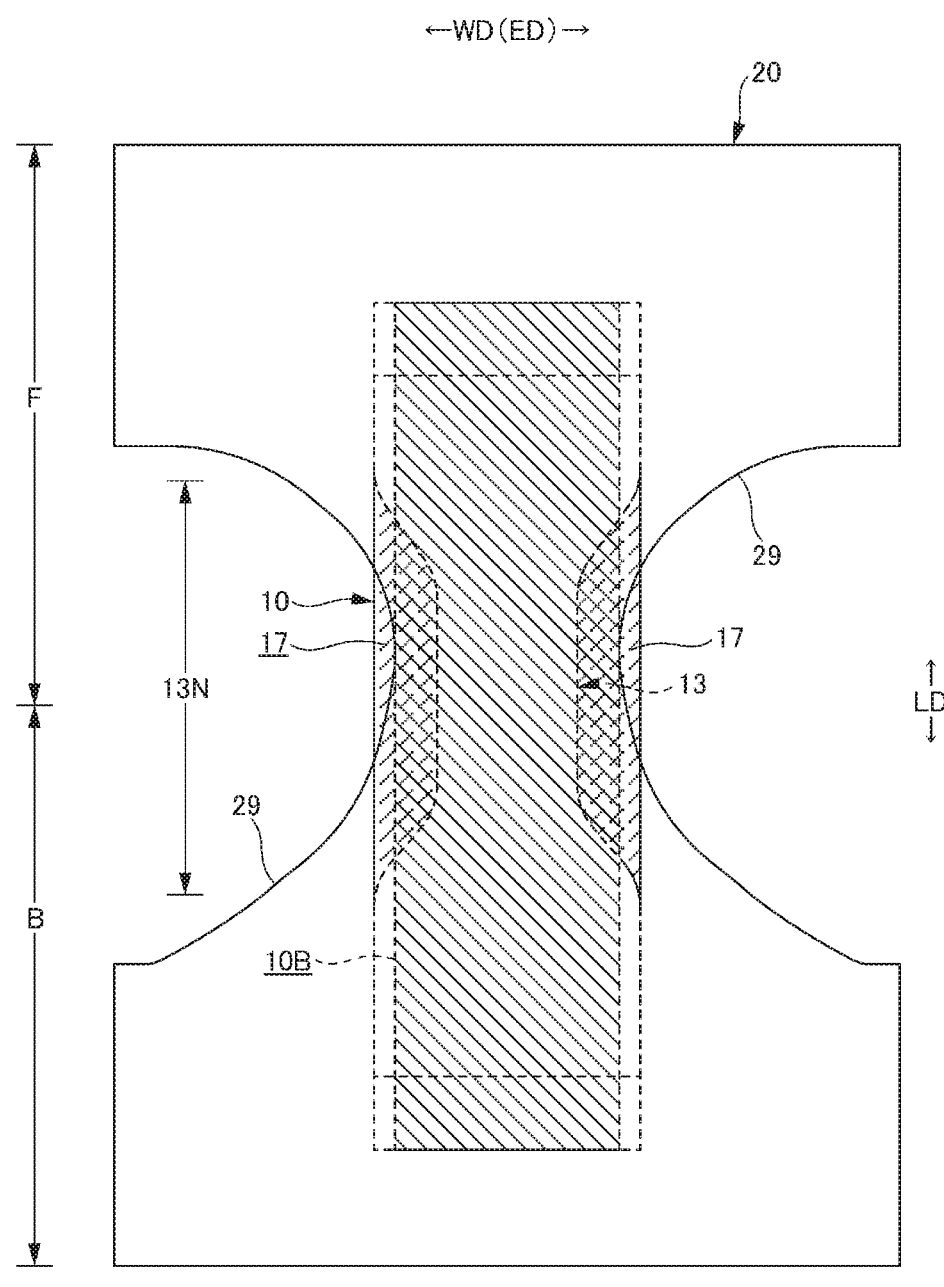

[FIG.4]
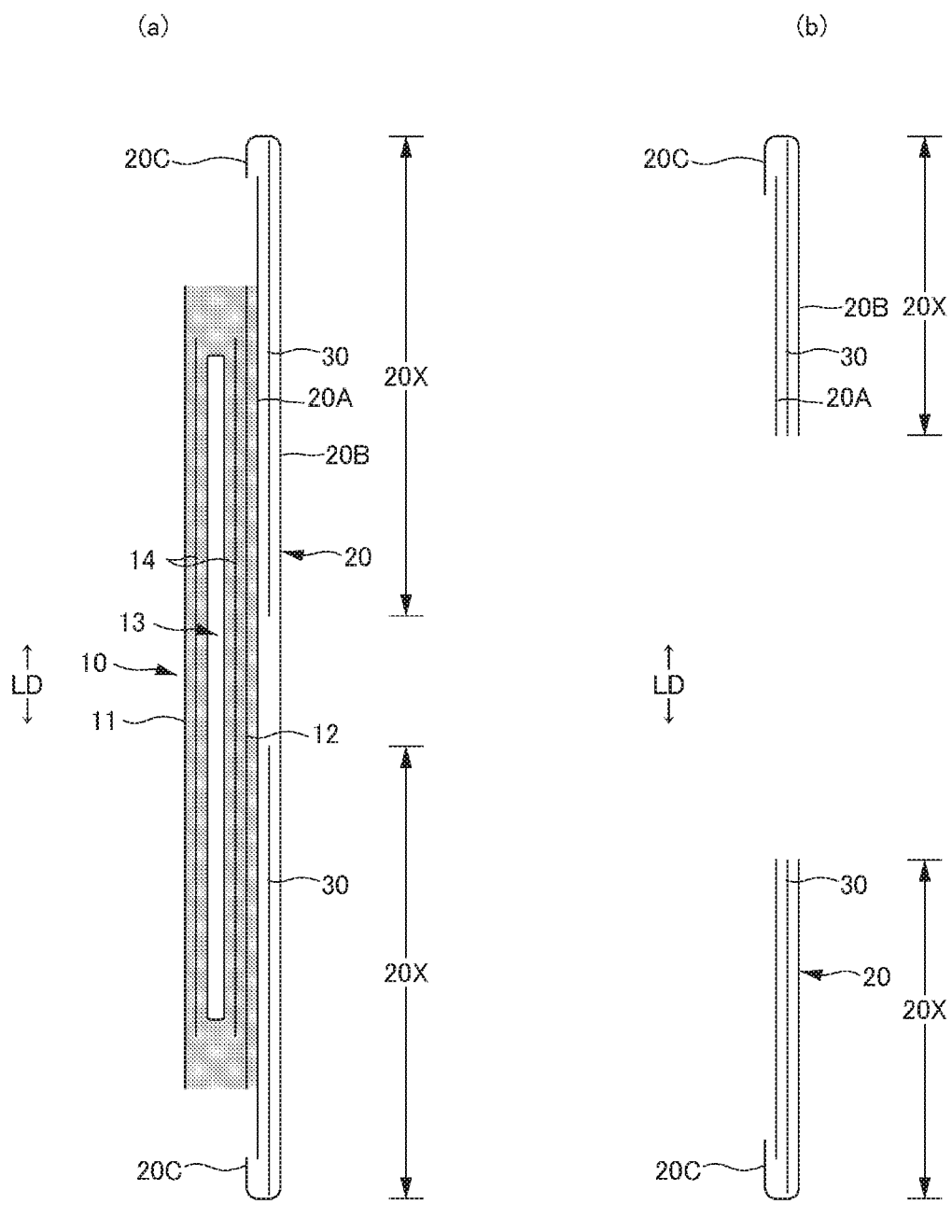

[FIG.5]
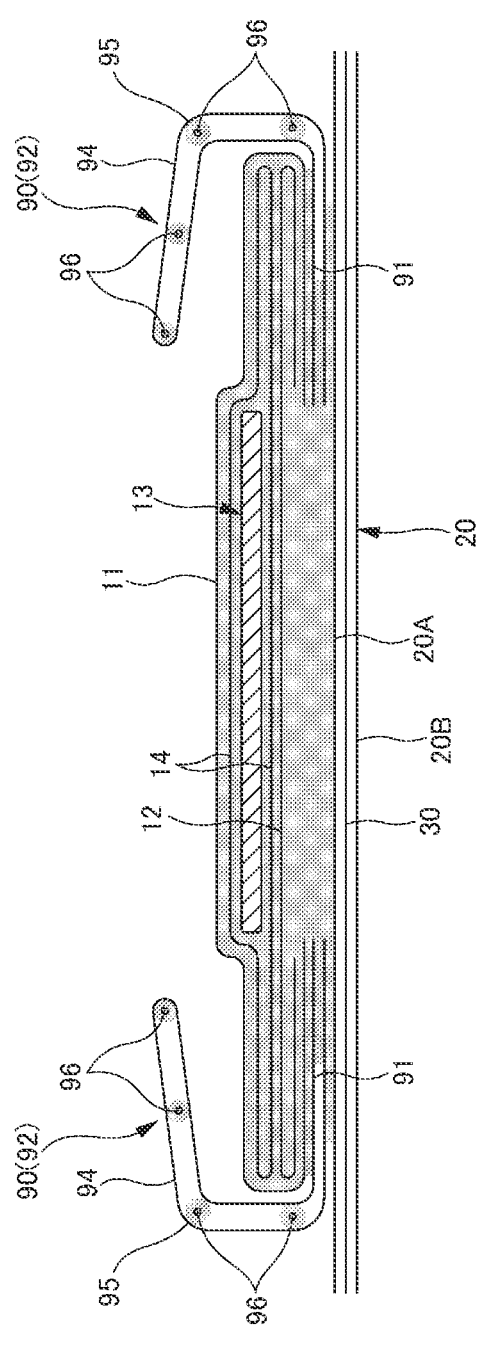

[FIG.6]
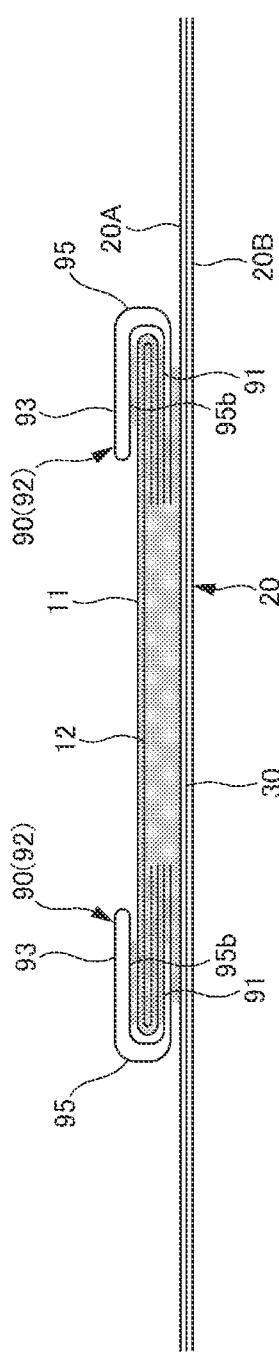

[FIG.7]
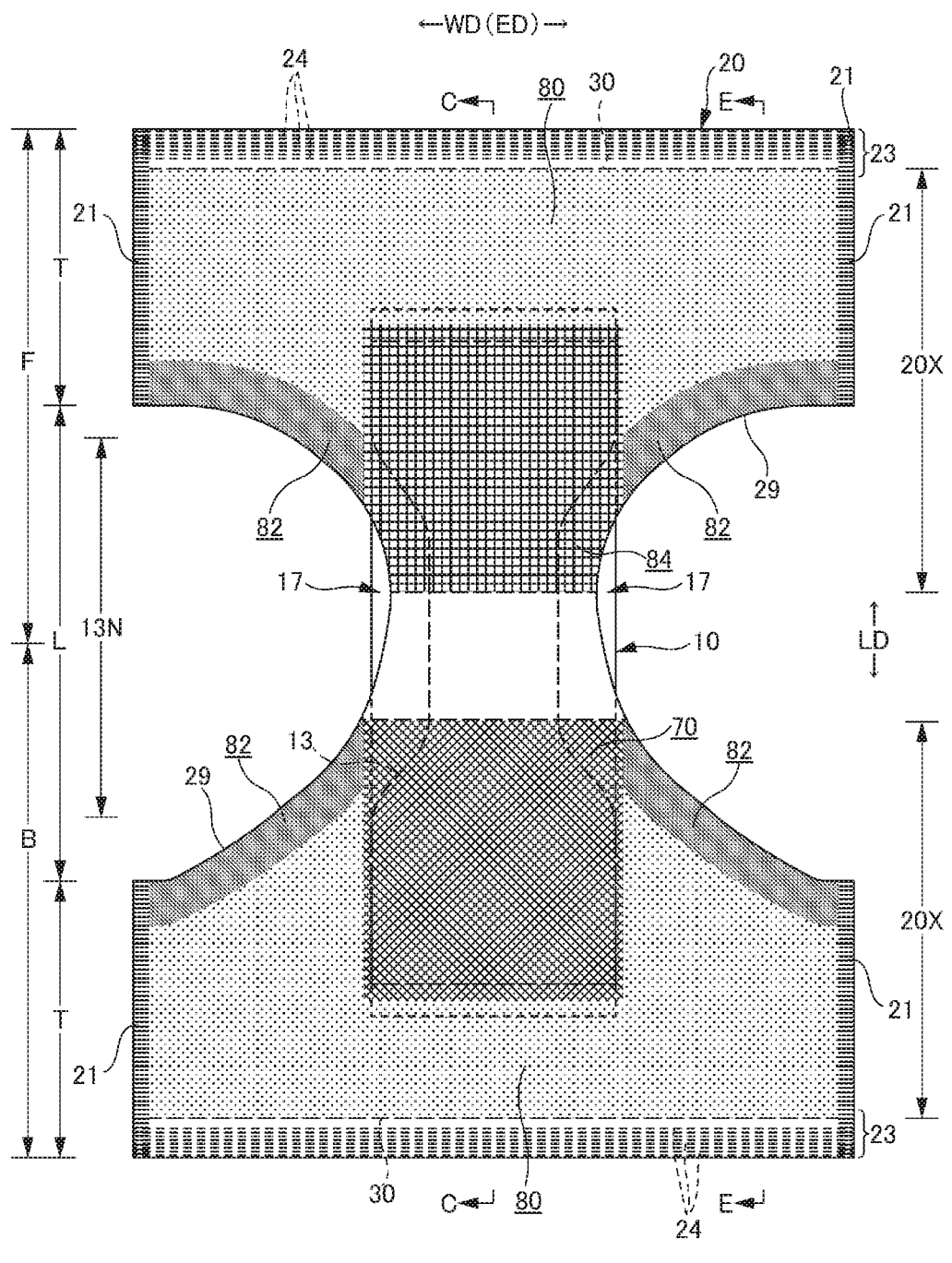

[FIG.8]
(a)                                 (b)
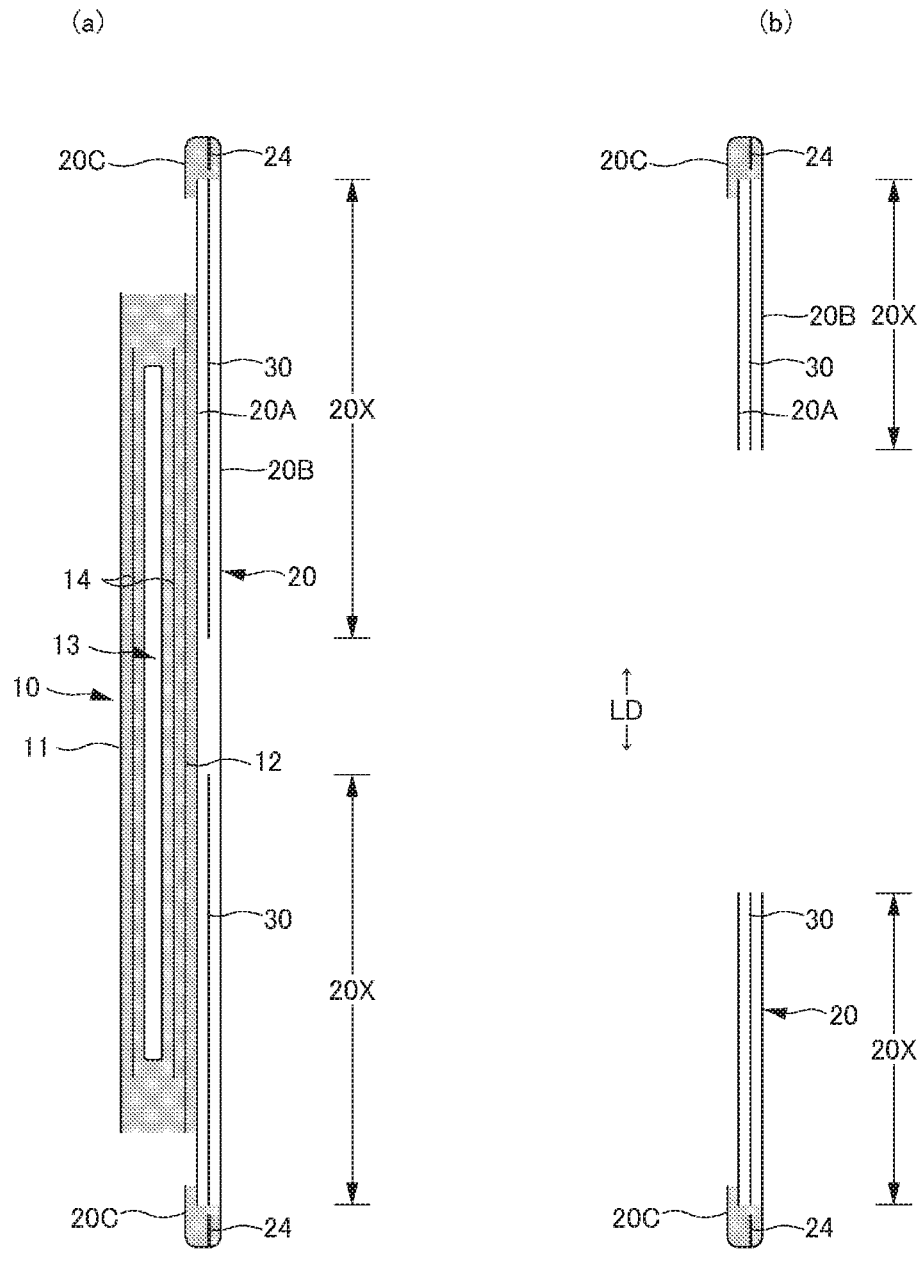

[FIG.9]
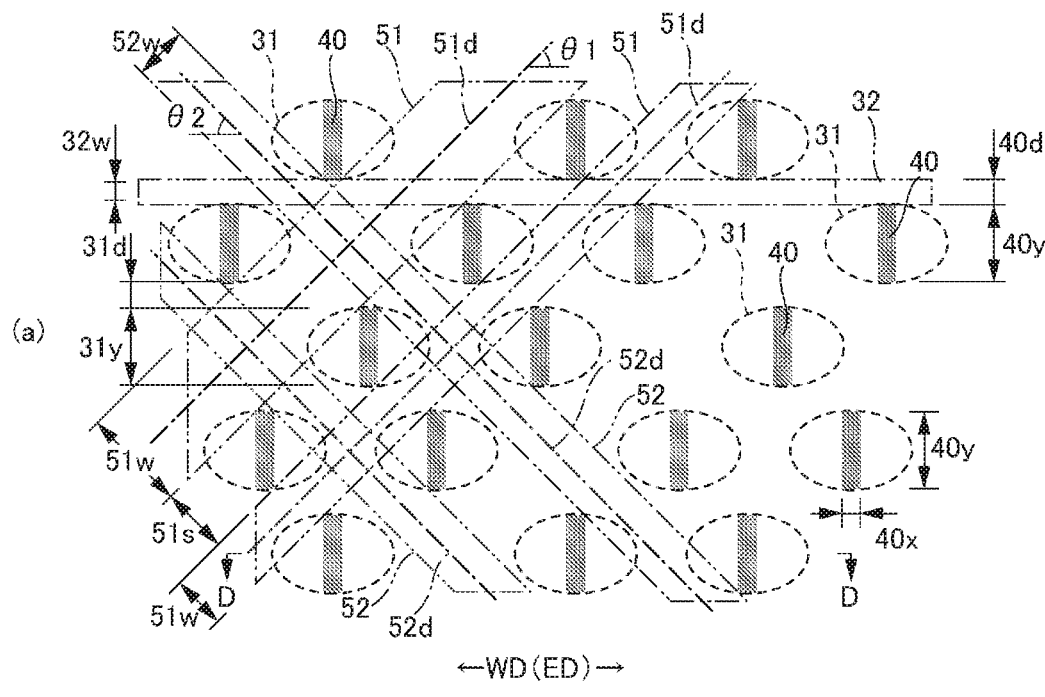
(a)
←WD(ED)→
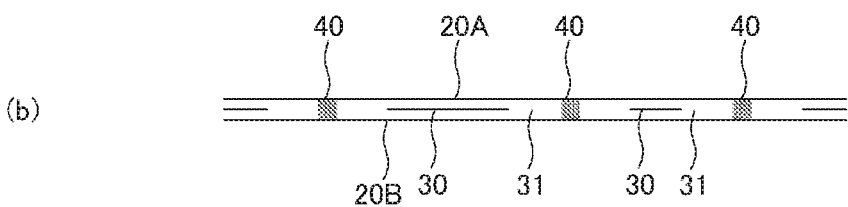
(b)
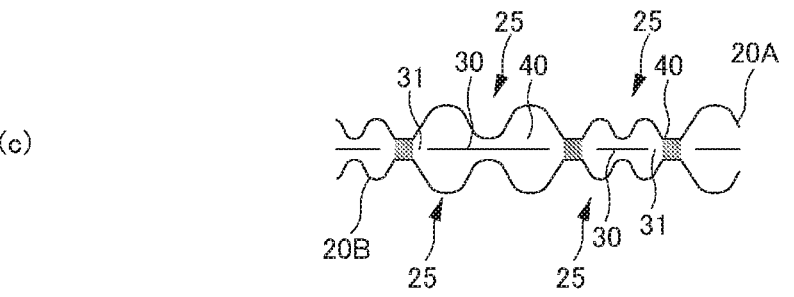
(c)
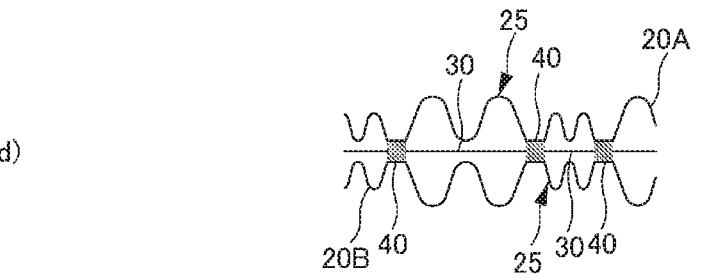
(d)

[FIG.10]
(a)
(b)
(c)
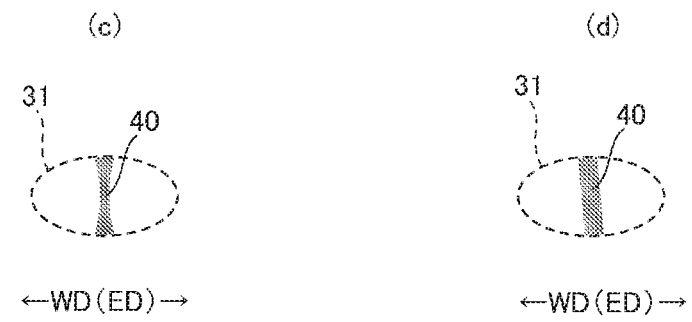
(d)

[FIG.11]
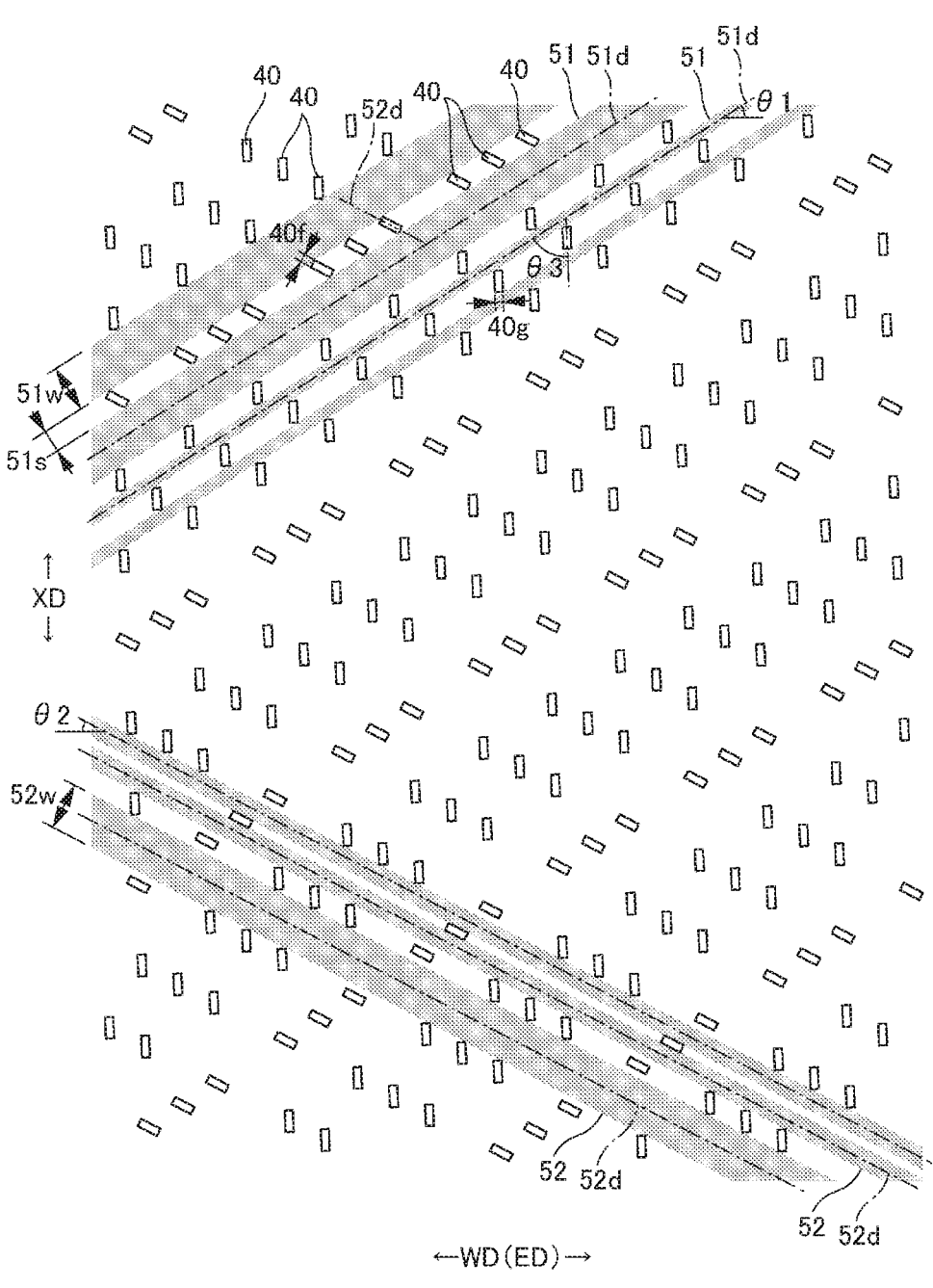

[FIG.12]
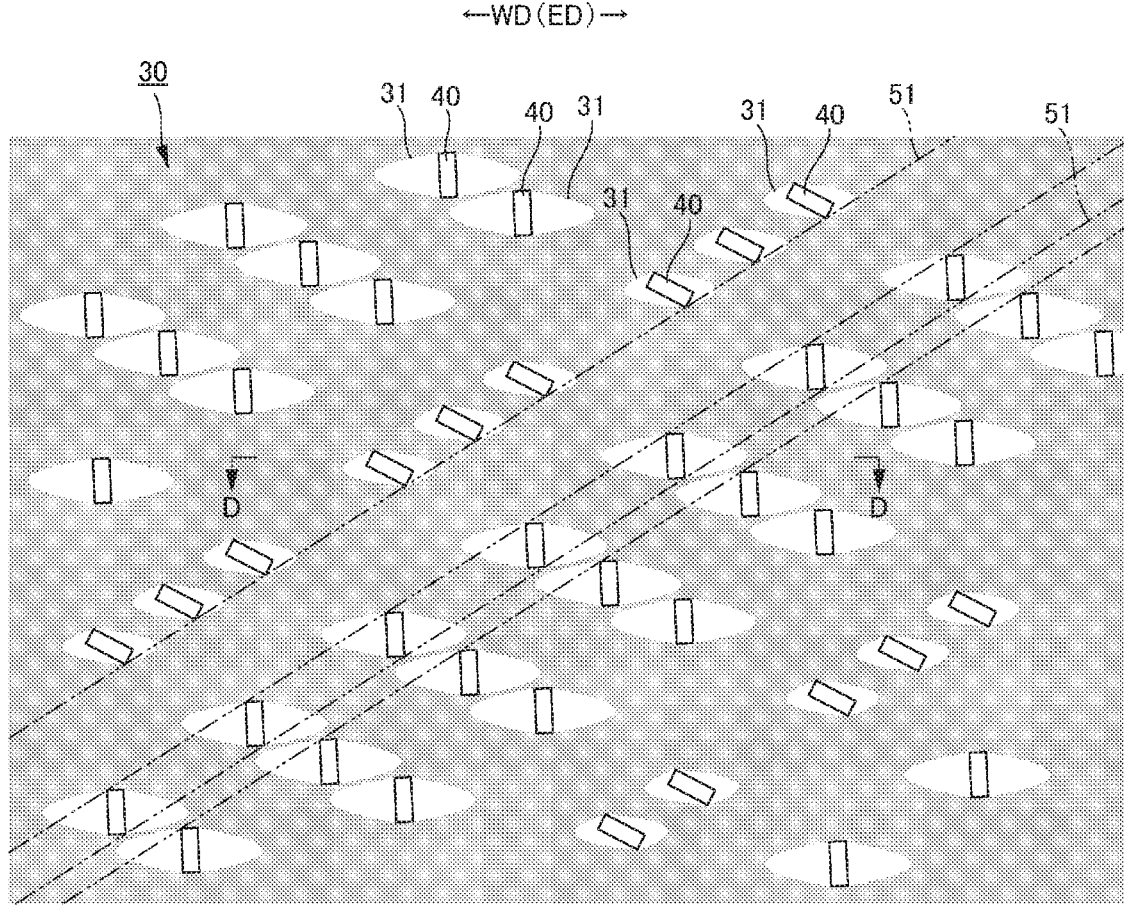

[FIG.13]
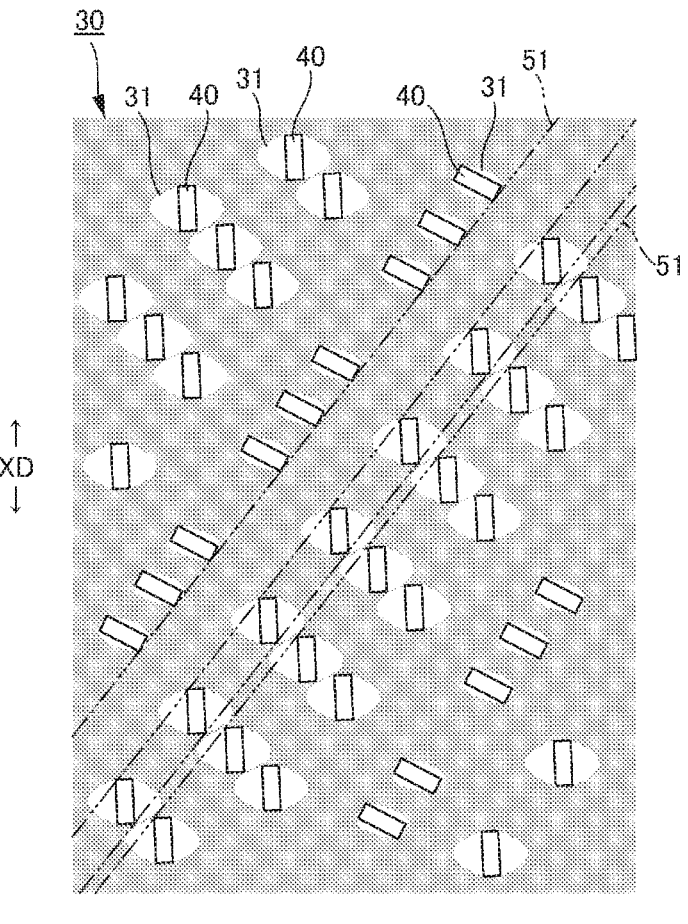

[FIG.14]
(a)
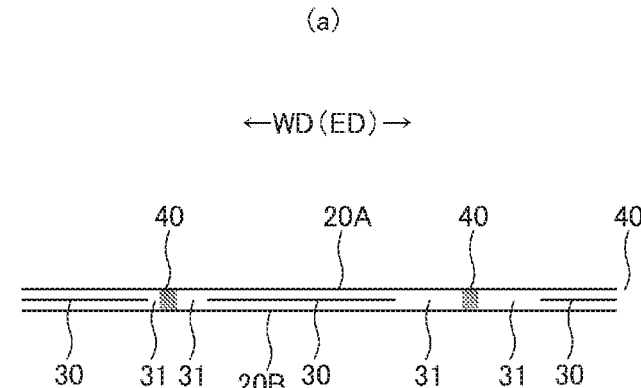
(b)
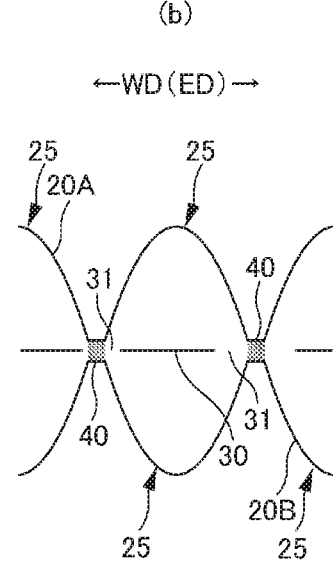

[FIG.15]
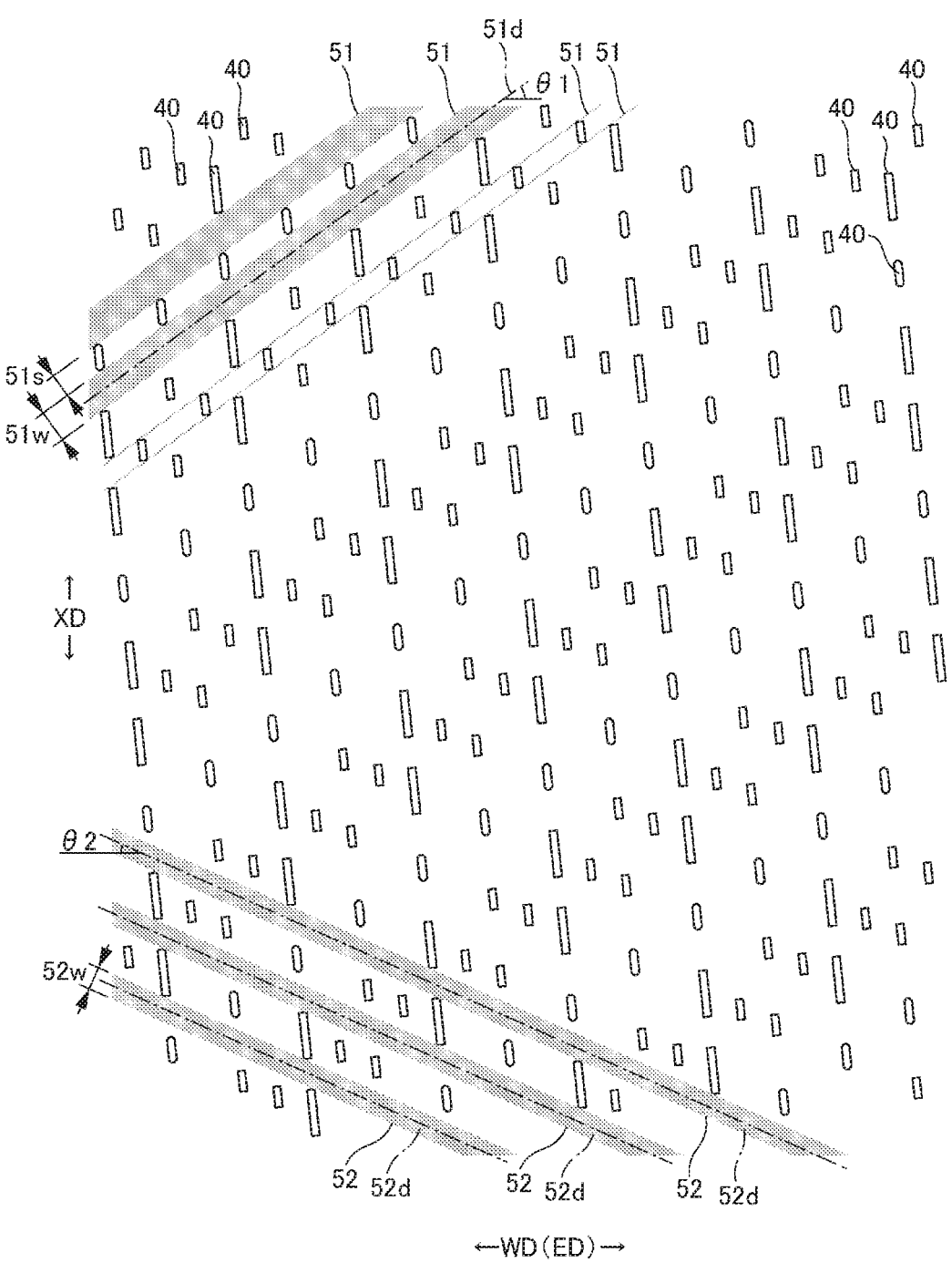

[FIG.16]
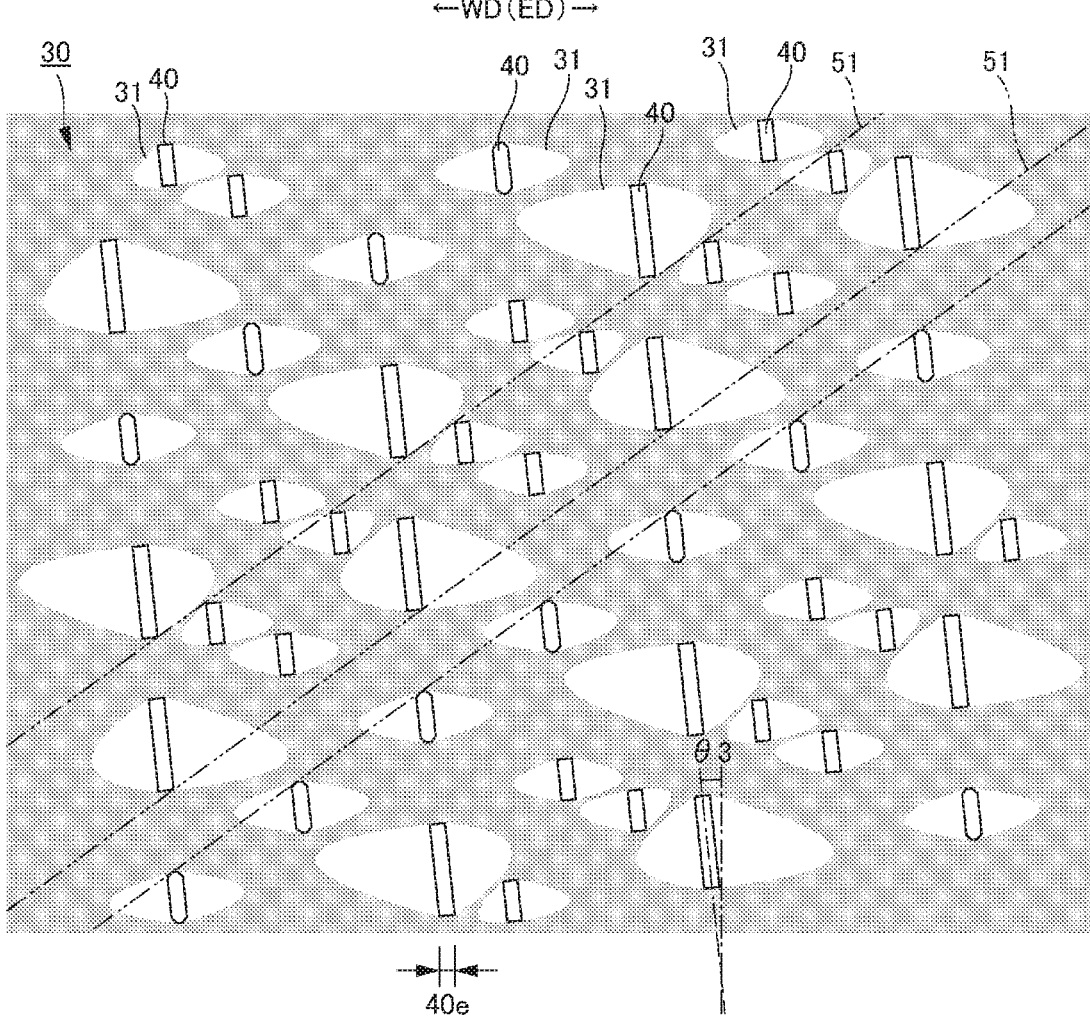

[FIG.17]
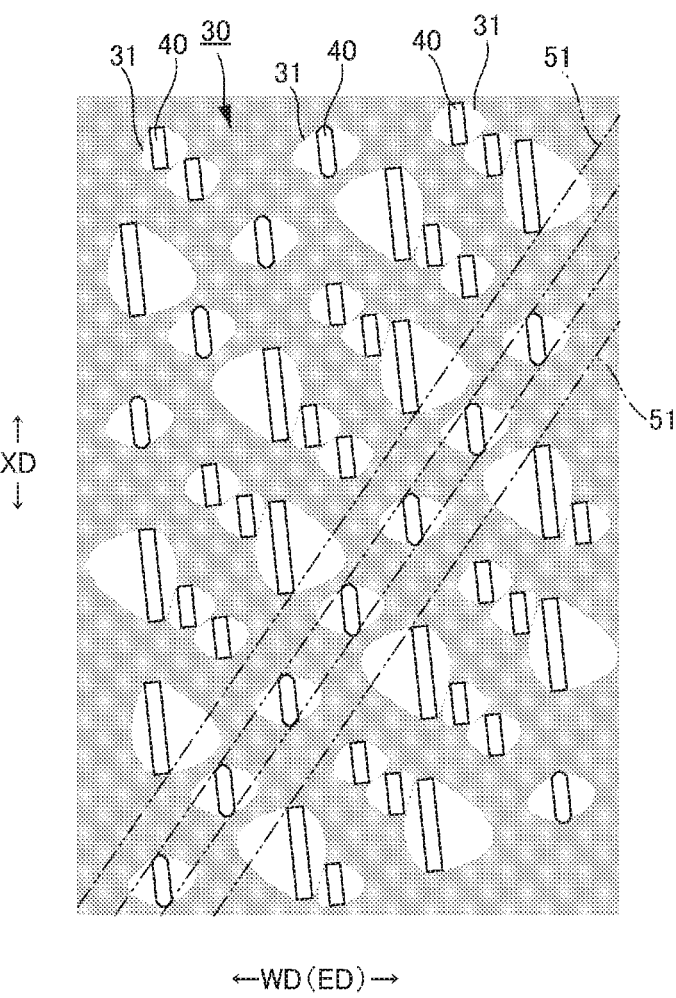
XD
←WD(ED)→

[FIG.18]
(a)
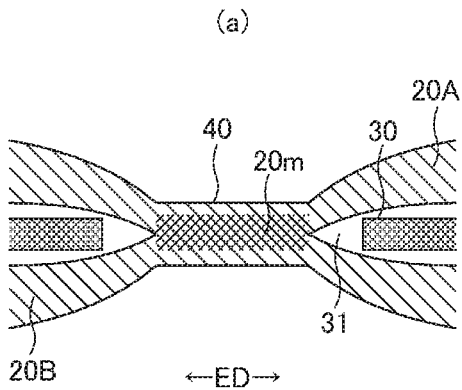
(b)
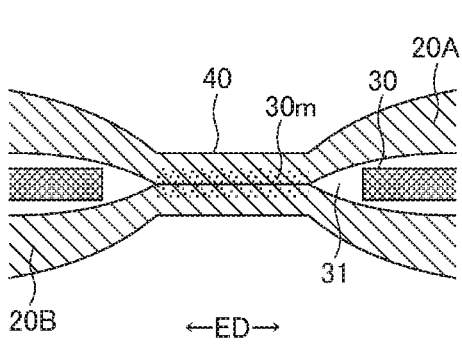
(c)
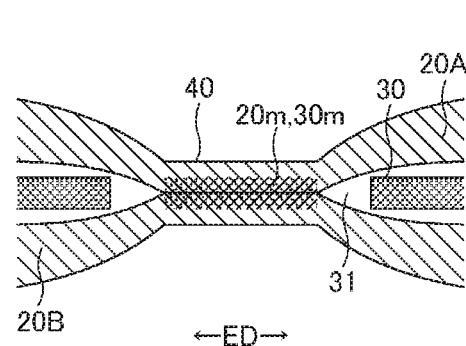

[FIG.19]
(a)
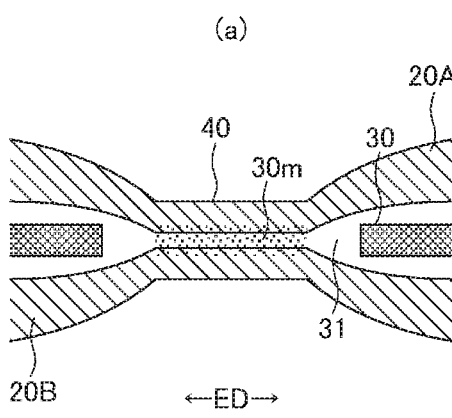
(b)
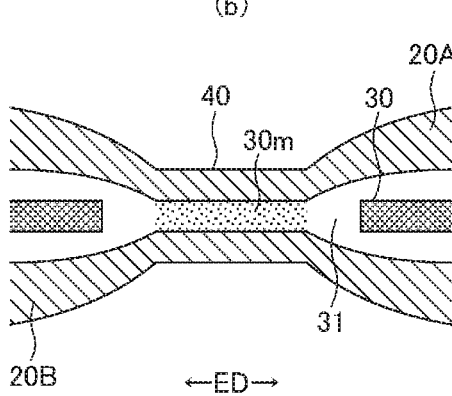
(c)
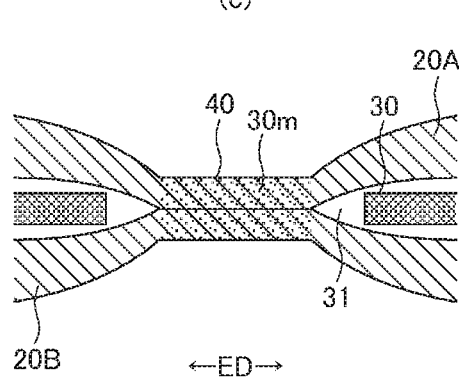

[FIG.20]
(a)
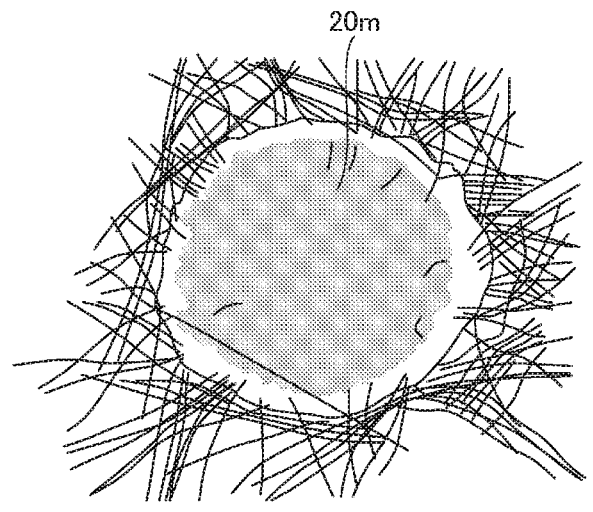
(b)
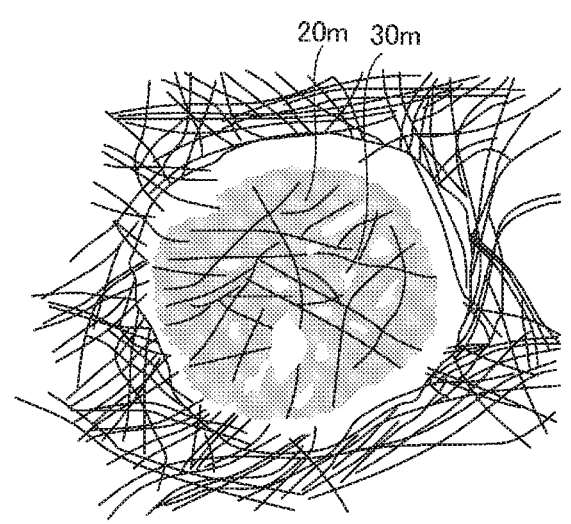

[FIG.21]
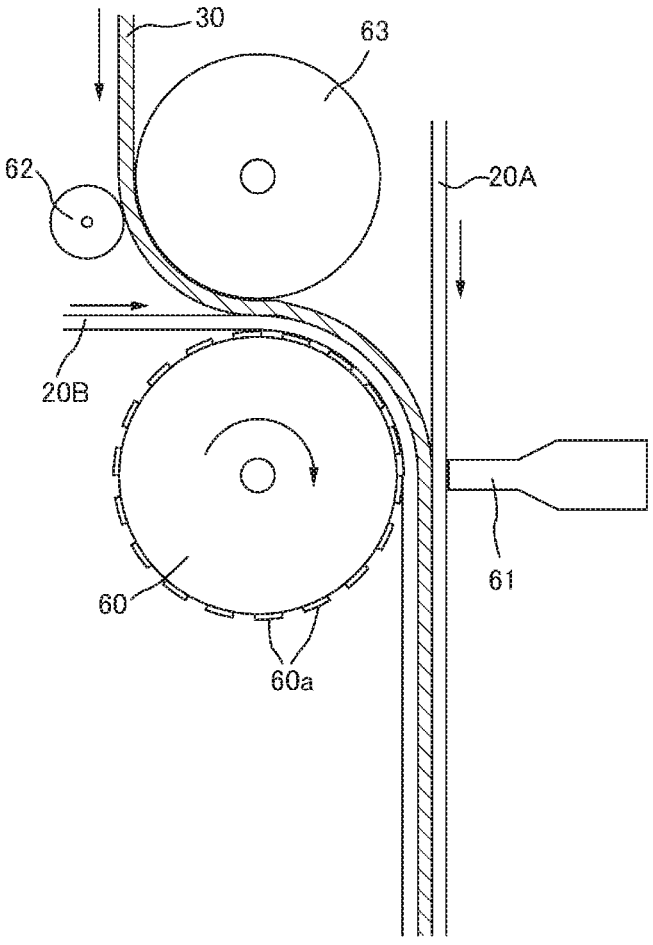

ELASTIC MEMBER AND DISPOSABLE WEARING ARTICLE INCLUDING ELASTIC MEMBER

TECHNICAL FIELD

The present invention relates to an elastic member having a stretchable structure in which an elastic sheet such as an elastic film is interposed between a first sheet layer and a second sheet layer, and a disposable wearing article including this elastic member.

BACKGROUND ART

In a disposable wearing article such as a disposable diaper, to improve fitting to a body surface, it is common to impart elasticity to an appropriate place such as around legs or around a waist. As a method of imparting elasticity, a method of attaching an elongated elastic member such as rubber thread in a state of being stretched in a longitudinal direction has been widely adopted. However, in the case of imparting elasticity at a certain width, a mode in which rubber threads are fixed in a state of being arranged side by side with an interval in the width has been adopted. In addition, as a method of obtaining an excellent surface fitting, a method of attaching an elastic sheet in a state of being stretched in a direction of imparting elasticity has been proposed. (For example, see Patent Literature 1 and Patent Literature 2).

The elastic member including the elastic sheet is obtained when an elastic film is stacked between a first sheet layer and a second sheet layer, and, in a state in which the elastic film is stretched in an stretchable direction, the first sheet layer and the second sheet layer are bonded by a plurality of dotted sheet joined portions arranged at intervals in the stretchable direction and a direction orthogonal thereto through joint holes formed in the elastic film. Further, in this elastic member, in a natural length state, as the elastic sheet contracts between the sheet joined portions, the intervals between the sheet joined portions decrease, and pleats are formed to extend in a direction intersecting the stretchable direction between the sheet joined portions in the first sheet layer and the second sheet layer. On the contrary, during stretching, as the elastic sheet stretches between the sheet joined portions, the intervals between the sheet joined portions and the pleats in the first sheet layer and the second sheet layer widen, and elastic stretching is allowed up to a fully unfolded state of the first sheet layer and the second sheet layer. A stretchable region by this elastic sheet is advantageous in that surface fitting is excellent, there is no bonding between the first sheet layer and the second sheet layer, and the elastic sheet, the structure is significantly flexible due to extremely little bonding between the first sheet layer and the second sheet layer, and the joint holes of the elastic sheet also contribute to improvement in air permeability.

Meanwhile, since the disposable wearing article is used together with underwear or as an alternative to underwear, the elastic member used for the disposable wearing article not only has functional requirements such as air permeability, fitting, and flexibility, but also requires appearance close to cloth.

However, in an elastic member including a conventional elastic sheet, sheet joined portions and joint holes of the elastic film are basically disposed in a non-directional pattern such as a staggered pattern. Thus, even when pleats are formed, an appearance is basically recognized as a plain appearance and aesthetics is poor.

CITATION LIST

Patent Literature

Patent Literature 1: JP 2016-189932 A
Patent Literature 2: JP 2015-204982 A

SUMMARY OF INVENTION

Technical Problem

Therefore, a main object of the invention is to improve the aesthetics of the elastic member including the elastic sheet.

Solution to Problem

An elastic member solving the above-mentioned problem and a disposable wearing article including this elastic member are as follows.
<First Aspect>
An elastic member having an elastic sheet stretchable structure in which an elastic sheet is interposed between a first sheet layer and a second sheet layer and the first sheet layer and the second sheet layer are bonded through joint holes penetrating the elastic sheet or via the elastic sheet at a plurality of sheet joined portions arranged at intervals, in which the first sheet layer and the second sheet layer are formed of a material having translucency and the elastic sheet is visually recognizable through the first sheet layer and the second sheet layer, a region having the elastic sheet stretchable structure has a stretchable region that contracts in an stretchable direction by contraction of the elastic sheet and is extensible in the stretchable direction, first non-joint bands linearly continuous along a first direction intersecting the stretchable direction at an acute angle are repeatedly present at intervals in a direction orthogonal to the first direction as non-joint bands in which a portion not having the sheet joined portions is continuous in an unfolded state in the stretchable region, a plurality of sheet joined portions and joint holes are provided at intervals between adjacent first non-joint bands in the stretchable region, and a unit structure including a plurality of first non-joint bands having different first widths determined as widths in the direction orthogonal to the first direction is repeatedly present in the direction orthogonal to the first direction in the stretchable region.
(Effect)
The inventors have found that in the elastic member including the elastic sheet, since transparency of a part having the elastic sheet decreases in a case in which the first sheet layer and the second sheet layer have translucency and the elastic sheet is visually recognizable through the first sheet layer and the second sheet layer as in the case of using a nonwoven fabric in the first sheet layer and the second sheet layer, a linear pattern can be effectively added by devising arrangement of the sheet joined portions and the joint holes. That is, as in the present aspect, when the unit structure including the plurality of first non-joint bands having different first widths is repeatedly present in the direction orthogonal to the first direction in the stretchable region, a similar magnitude change in width is formed in a continuous portion of the elastic sheet inside the first non-joint bands. That is, when the width of the first non-joint bands is narrow, the width of the continuous portion of the elastic sheet on the inside is narrowed. Further, when the width of the first non-joint bands is wide, the width of the continuous portion of the elastic sheet on the inside is widened. Further, when there is a change in width in the direction orthogonal to the first direction in the continuous portion of the elastic sheet in the first non-joint bands, both the continuous portion of the elastic sheet in first non-joint bands having a wide width and the continuous portion of the elastic sheet in first non-joint bands having a narrow width are visually emphasized. As a result, regardless of whether the stretchable region is in the natural length state or in the worn state stretched to some extent, an appearance having beautiful oblique stripe patterns is exhibited. In addition, in a state of being contracted to some extent, for example, in the natural length state (product state), a size of the contraction pleats in the first non-joint bands changes according to the first width of the first non-joint bands, and thus an oblique stripe pattern appears more clearly due to an influence of the contraction pleats.

<Second Aspect>

The elastic member according to first aspect, in which a maximum value of the first widths in the first non-joint bands is a maximum value of widths in a direction orthogonal to a continuous direction in all the non-joint bands.

(Effect)

Even if an oblique stripe pattern along the first direction due to the contraction pleats of the first non-joint bands and the continuous portion of the elastic sheet therein appears, when an oblique stripe pattern along another oblique direction is more strongly visually recognized in the same stretchable region, there is concern that the oblique stripe pattern due to the contraction pleats of the first non-joint bands and the continuous portion of the elastic sheet therein becomes inconspicuous. On the other hand, a configuration as in the present aspect is preferable since the oblique stripe pattern due to the contraction pleats of the first non-joint bands and the continuous portion of the elastic sheet inside thereof is more strongly visually recognized in the stretchable region.

<Third Aspect>

The elastic member according to the first or second aspect, in which in the unit structure, the maximum value of the first widths in the first non-joint bands is smaller than a maximum value of a first interval determined as an interval in the direction orthogonal to the first direction in the adjacent first non-joint bands.

(Effect)

In this way, by forming a wide interval portion in the unit structure, the oblique stripe pattern due to the contraction pleats of the first non-joint bands and the continuous portion of the elastic sheet inside thereof is more strongly visually recognized, which is preferable.

<Fourth Aspect>

The elastic member according to any one of the first to third aspects, in which in the stretchable region, second non-joint bands linearly continuous along a second direction intersecting the stretchable direction at an acute angle other than the first direction is repeatedly present as the non-joint bands at intervals in a direction orthogonal to the second direction and all second widths determined as widths in the direction orthogonal to the second direction in the second non-joint bands are the same, or the second non-joint bands are not included.

(Effect)

Even if an oblique stripe pattern along the first direction due to the contraction pleats of the first non-joint bands and the continuous portion of the elastic sheet therein appears, when an oblique stripe pattern along another oblique direction is more strongly visually recognized in the same stretchable region, there is concern that the oblique stripe pattern due to the contraction pleats of the first non-joint bands and the continuous portion of the elastic sheet therein becomes inconspicuous. On the other hand, a configuration as in the present aspect is preferable since the oblique stripe pattern due to the contraction pleats of the first non-joint bands and the continuous portion of the elastic sheet inside thereof is more strongly visually recognized in the stretchable region.

<Fifth Aspect>

The elastic member according to the fourth aspect, in which the non-joint bands are formed in an oblique lattice shape in the stretchable region, the first non-joint bands correspond to portions continuous in one direction in the non-joint bands having the oblique lattice shape, the second non-joint bands correspond to portions continuous in another direction in the non-joint bands having the oblique lattice shape, the first direction and the second direction are opposite to each other in terms of inclination with respect to the stretchable direction, and each of acute intersecting angles between the first and second directions and the stretchable direction is 5 to 45 degrees in the unfolded state of the stretchable region.

(Effect)

Even in the case of having the non-joint bands having the oblique lattice shape as in the present aspect, by combination with the fourth aspect, the oblique stripe pattern due to the contraction pleats of the first non-joint bands and the continuous portion of the elastic sheet inside thereof is more strongly visually recognized. Further, when the acute intersecting angles between the first and second directions and the stretchable direction are 5 to 45 degrees, sufficient elasticity in the stretchable region can be ensured.

<Sixth Aspect>

The elastic member according to the fifth aspect, in which all the sheet joined portions in the stretchable region have an elongated shape in which an acute intersecting angle between a longitudinal direction and a direction orthogonal to the stretchable direction is within 10 degrees and a maximum dimension in the stretchable direction is 0.1 to 0.4 mm.

(Effect)

In the case of forming the first non-joint bands, the sheet joined portions are aligned in the first direction between the adjacent first non-joint bands. In this case, when all the sheet joined portions are formed in an elongated shape in the direction orthogonal to the stretchable direction as in the present aspect, it is possible to ensure a large dimension of the first non-joint bands in the stretchable direction, and to suppress a decrease in elasticity.

<Seventh Aspect>

The elastic member according to the fifth aspect, in which the unit structure includes a plurality of first wide non-joint bands having a maximum first width and a plurality of first narrow non-joint bands having a narrower first width than the maximum first width adjacent to each other in the direction orthogonal to the first direction, sheet joined portions having an elongated shape in which an acute intersecting angle between a longitudinal direction and the second direction is within 5 degrees and a dimension in a direction orthogonal to the longitudinal direction is 0.1 to 0.4 mm are aligned at intervals in the first direction between the adjacent first wide non-joint bands, and sheet joined portions having an elongated shape in which an acute intersecting angle between a longitudinal direction and the first direction is 45 degrees or more and a dimension in a direction orthogonal to the longitudinal direction is 0.1 to 0.4 mm are aligned at intervals in the first direction between the adjacent first narrow non-joint bands.

(Effect)

By such a shape and arrangement of the sheet joined portions, the contraction pleats of the first non-joint bands and the continuous portion of the elastic sheet therein are particularly visually emphasized using the area of fewer sheet joined portions, which is preferable.

<Eighth Aspect>

An underpants-type disposable wearing article including:

an integrated outer member covering from a front body to a back body or outer members separately provided for the front body and the back body;

an inner member attached to an intermediate portion of the outer member in a width direction to extend to both front and back sides of a crotch portion;

side seal portions in which both side portions of the outer member in the front body and both side portions of the outer member in the back body are bonded to each other; and a waist opening and a pair of right and left leg openings, in which the outer member in at least one of the front body and the back body is an elastic member having the elastic sheet stretchable structure according to any one of the first to seventh aspects over a range in the width direction corresponding to a space between the side seal portions at least in a partial range in a front-back direction so that an stretchable direction of a stretchable region thereof corresponds to the width direction.

(Effect)

The elastic member described above is suitable for the outer member of the underpants-type disposable wearing article as in the present aspect.

Advantageous Effects of Invention

The invention is advantageous in that aesthetics of the elastic member including the elastic sheet is improved.

BRIEF DESCRIPTION OF DRAWINGS

FIG. 1 is a plan view (internal surface side) of an underpants-type disposable diaper in an unfolded state.

FIG. 2 is a plan view (external surface side) of the underpants-type disposable diaper in the unfolded state.

FIG. 3 is a plan view illustrating only a main part of the underpants-type disposable diaper in the unfolded state.

FIG. 4(*a*) is a cross-sectional view taken along C-C line of FIG. 1, and FIG. 4(*b*) is a cross-sectional view taken along E-E line of FIG. 1.

FIG. 5 is a cross-sectional view taken along A-A line of FIG. 1.

FIG. 6 is a cross-sectional view taken along B-B line of FIG. 1.

FIG. 7 is a plan view (external surface side) of the underpants-type disposable diaper in the unfolded state.

FIG. 8(*a*) is a cross-sectional view taken along C-C line of FIG. 7, and FIG. 8(*b*) is a cross-sectional view taken along E-E line of FIG. 7.

FIG. 9(*a*) is a plan view of a main part of a stretchable region, FIG. 9(*b*) is a cross-sectional view taken along D-D line of FIG. 9(*a*), FIG. 9(*c*) is a cross-sectional view in a worn state, and FIG. 9(*d*) is a cross-sectional view in a natural length state.

FIG. 10 is a plan view illustrating various shapes of the sheet joined portions.

FIG. 11 is a plan view of the stretchable region in the unfolded state.

FIG. 12 is an enlarged plan view illustrating a main part of the stretchable region in the unfolded state.

FIG. 13 is an enlarged plan view illustrating a main part of the stretchable region in the natural length state.

FIG. 14(*a*) is a cross-sectional view taken along D-D line of FIG. 12, and FIG. 14(*b*) is a cross-sectional view in the natural length state.

FIG. 15 is a plan view of the stretchable region in the unfolded state.

FIG. 16 is an enlarged plan view illustrating the main part of the stretchable region in the unfolded state.

FIG. 17 is an enlarged plan view illustrating the main part of the stretchable region in the natural length state.

FIG. 18 is a cross-sectional view schematically illustrating a cross section of a main part of an outer member stretched to some extent.

FIG. 19 is a cross-sectional view schematically illustrating a cross section of the main part of the outer member stretched to some extent.

FIG. 20(*a*) is a trace view of a plane photograph of sheet joined portions formed in a first welding mode, and FIG. 20(*b*) is a trace view of a plane photograph of sheet joined portions formed in a third welding mode.

FIG. 21 is a schematic view of an ultrasonic sealing device.

DESCRIPTION OF EMBODIMENTS

Hereinafter, a detailed description will be given of an elastic member and a disposable wearing article based on an example of an underpants-type disposable diaper illustrated in accompanying drawings. Incidentally, a dotted pattern portion in a cross-sectional view illustrates bonding means such as a hotmelt adhesive.

FIG. 1 to FIG. 6 illustrate the underpants-type disposable diaper. A reference character LD (longitudinal direction) denotes a front-back direction, and a reference character WD denotes a width direction. The underpants-type disposable diaper (hereinafter also simply referred to as a diaper) includes an outer member 20 forming a front body F and a back body B, and an inner member 10 fixed to and integrated with an inner surface of the outer member 20, and the inner member 10 is formed by interposing an absorbent body 13 between a liquid pervious top sheet 11 and a liquid impervious sheet 12. In manufacturing, after a back surface of the inner member 10 is bonded to the inner surface (upper surface) of the outer member 20 by bonding means such as a hotmelt adhesive, the inner member 10 and the outer member 20 are folded at a center in the front-back direction LD (longitudinal direction) corresponding to a boundary between the front body F and the back body B, and both side portions thereof are bonded to each other by thermal welding or the hotmelt adhesive to form side seal portions 21, thereby obtaining the underpants-type disposable diaper in which a waist opening and a pair of right and left leg openings are formed.

(Structure Example of Inner Member)

As illustrated in FIG. 4 to FIG. 6, the inner member 10 has a structure in which the absorbent body 13 is interposed between the top sheet 11 and the liquid impervious sheet 12 made of polyethylene, etc. and absorbs and holds excretion fluid passing through the top sheet 11. A planar shape of the inner member 10 is not particularly limited. However, a substantially rectangular shape is generally adopted as illustrated in FIG. 1.

As the top sheet 11 that covers the front surface side (skin side) of the absorbent body 13, a perforated or non-perforated nonwoven fabric, a porous plastic sheet, etc. is preferably used. As a material fiber constituting the nonwoven fabric, it is possible to adopt a regenerated fiber such as rayon and cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunlace method, a spunbond method, a thermal bond method, a meltblown method, a needle punch method, etc.

As the liquid impervious sheet 12 covering the back surface side (non-skin contact side) of the absorbent body 13, a liquid impervious plastic sheet such as polyethylene or polypropylene may be used. In particular, a sheet having a moisture penetration property may be preferably used from a viewpoint of preventing stuffiness. Examples thereof include a microporous sheet obtained by melt-kneading an inorganic filler in a polyolefin resin such as polyethylene or polypropylene to form a sheet, and then stretching the sheet in a uniaxial or biaxial direction.

As the absorbent body 13, it is possible to use a known one, for example, a pulp fiber stack, an assembly of filaments of cellulose acetate, etc., or a nonwoven fabric-based body mixed with a high-absorbent polymer as necessary or fixed. To hold the shape and the polymer, the absorbent body 13 can be wrapped in a package sheet 14 having a liquid pervious and liquid retaining property such as crepe paper as necessary.

The absorbent body 13 is formed into a substantially hourglass shape having a narrower portion 13N narrower than both front and back sides at a crotch portion. A size of the narrower portion 13N can be determined as appropriate. A length of the narrower portion 13N in the front-back direction can be set to about 20 to 50% of a maximum length of the diaper, and a width of a narrowest portion thereof can be set to about 40 to 60% of a maximum width of the absorbent body 13. In the case of having such a narrower portion 13N, when the planar shape of the inner member 10 is substantially rectangular, non-absorbent body side portions 17 not having the absorbent body 13 are formed at a portion corresponding to the narrower portion 13N of the absorbent body 13 in the inner member 10.

The liquid impervious sheet 12 is folded back to the back surface side on both sides of the absorbent body 13 in the width direction together with the top sheet 11. As this liquid impervious sheet 12, it is desirable to use an opaque sheet so that brown color of excreta or urine is not seen. As opacification, a pigment or a filler such as calcium carbonate, titanium oxide, zinc oxide, white carbon, clay, talc, or barium sulfate added to plastic and formed into a film is preferably used.

Three-dimensional gathers 90 fit around the legs are formed on both side portions of the inner member 10. As illustrated in FIG. 5 and FIG. 6, each of the three-dimensional gathers 90 includes a fixed portion 91 fixed to a side portion of the back surface of the inner member 10, a main unit section 92 stretchable from the fixed portion 91 up to a side portion of the front surface of the inner member 10 through a side of the inner member 10, a fallen portion 93 formed by front and back end portions of the main unit section 92 fixed to the side portion of the front surface of the inner member 10 (top sheet 11 in the illustrated example) in a fallen state using a hotmelt adhesive 95b, etc., and a free portion 94 formed between parts of the fallen portion 93 which are not fixed. Each of these portions is formed of a gather sheet 95 that is a duplicate sheet obtained by folding a sheet such as a nonwoven fabric. The gather sheet 95 is attached over the entire inner member 10 in the front-back direction, the fallen portion 93 is provided on the front side and the back side of each of the non-absorbent body side portions 17, and the free portion 94 extends to both the front and back sides of the non-absorbent body side portion 17. In addition, between the double gather sheets 95, gather elastic members 96 are disposed at tip portions of the free portion. As illustrated in FIG. 5, the gather elastic members 96 are for raising the free portion 94 by an elastic contraction force in a product state.

A fixing structure of the gather elastic members 96 and the gather sheets 95 is not particularly limited. For example, as in an example illustrated in FIG. 5 and FIG. 6, it is possible to adopt a structure described in the following. In portions other than the fallen portion 93, the gather elastic members 96 are attached and fixed to the gather sheets 95 through a hotmelt adhesive at positions of the gather elastic members 96, and facing surfaces of the gather sheets 95 are bonded to each other. However, in the fallen portion 93, the hotmelt adhesive is not present at the positions of the gather elastic members 96. Therefore, the gather elastic members 96 and the gather sheets 95 are not attached to each other, and the facing surfaces of the gather sheets 95 are not bonded to each other at positions having the gather elastic members 96.

As the gather elastic members 96, it is possible to use normally used materials such as polystyrene-based rubber, polyolefin-based rubber, polyurethane-based rubber, polyester-based rubber, polyurethane, polyethylene, polystyrene, styrene-butadiene copolymer, silicone, polyester, etc. In addition, to make it difficult to see from the outside, it is preferable that a fineness is set to 925 dtex or less, a tension is set to 150 to 350%, and an interval is set to 7.0 mm or less. Incidentally, as the gather elastic members 96, it is possible to use a tape-like member having a certain width in addition to an elongated member as in the illustrated example.

As a material fiber constituting the gather sheets 95 described above, similarly to the top sheet 11, it is possible to adopt a regenerated fiber such as rayon or cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunbond method, a thermal bond method, a meltblown method, a needle punch method, etc. However, in particular, in order to prevent stuffiness, it is preferable to use a nonwoven fabric that suppresses a basis weight and has excellent air permeability. Further, with regard to the gather sheets 95, to prevent passage of urine, etc., prevent a rash, and enhance a feel to a skin (dry feeling), it is preferable to use a water repellent nonwoven fabric coated with a silicone-based, paraffin metal-based, or alkylchromic chloride-based water repellent agent, etc.

As illustrated in FIG. 3 to FIG. 6, the back surface of the inner member 10 is bonded to the inner surface of the outer member 20 by a hotmelt adhesive, etc. in an inner/outer fixing region 10B (shaded region). The inner/outer fixing region 10B may be determined as appropriate and may correspond to almost the entire inner member 10 in a width direction WD. However, it is preferable that both ends in the width direction are not fixed to the outer member 20.

(Structure Example of Outer Member)

The outer member 20 includes at least the lower torso portion T of the front body F and the lower torso portion T of the back body B, and further includes an intermediate portion L corresponding to a range in the front-back direction between the lower torso portion T of the front body F and the lower torso portion T of the back body B in the illustrated example. Referring to the outer member 20, as in the illustrated example, in a crotch portion, side edges of the outer member 20 may be located on a central side of side edges of the inner member 10 in the width direction or located on an outer side thereof in the width direction.

Further, the outer member 20 of the illustrated example has an elastic sheet stretchable structure 20X in which an elastic sheet 30 is interposed between the translucent first sheet layer 20A and second sheet layer 20B as illustrated in FIG. 2 and FIG. 4 to FIG. 6 except for a middle of the intermediate portion L in the front-back direction and the first sheet layer 20A and the second sheet layer 20B are bonded through joint holes 31 penetrating the elastic sheet 30 at a plurality of sheet joined portions 40 arranged at intervals as illustrated in FIG. 9. Further, a region having this elastic sheet stretchable structure includes a stretchable region that contracts in the width direction by contraction of the elastic sheet and is extensible in the width direction (that is, the stretchable direction ED is the width direction WD of the diaper).

The first sheet layer 20A and the second sheet layer 20B may be indirectly bonded through the elastic sheet 30 instead of through the joint holes 31 of the elastic sheet 30. A planar shape of the outer member 20 is formed by concave around-leg lines 29 so that both side edges of the intermediate portion L in the width direction form leg openings, respectively, and has a shape similar to an hourglass as a whole. The outer member 20 may be formed separately in the front body F and the back body B, and both bodies may be disposed to be separated in the front-back direction LD of the diaper at the crotch portion.

An embodiment illustrated in FIG. 1 and FIG. 2 is an embodiment in which the elastic sheet stretchable structure 20X extends up to waist end portions 23. However, if necessary, for example, if tightening of the waist end portions 23 is insufficient when the elastic sheet stretchable structure 20X is used for the waist end portions 23, the stretchable structure may be provided by conventional elongated waist portion elastic members 24 without providing the elastic sheet stretchable structure 20X in the waist end portions 23 as illustrated in FIG. 7 and FIG. 8. The waist portion elastic members 24 are elongated elastic members such as a plurality of rubber threads disposed at intervals in the front-back direction LD, and apply a stretching force to tighten a waist of a body. The waist portion elastic members 24 are not disposed substantially in a bundle at close intervals, and three or more waist portion elastic members 24, preferably five or more waist portion elastic members 24 are disposed at intervals of about 3 to 8 mm in the front-back direction to form a predetermined stretchable zone. A stretch rate the waist portion elastic members 24 at the time of fixing can be determined as appropriate, and may be set to about 230 to 320% for a normal adult. As the waist portion elastic members 24, rubber threads are used in the illustrated example. However, other elongated elastic members such as flat rubber may be used. Although not illustrated, the elastic sheet 30 may be provided at the waist end portions 23, and the elongated waist portion elastic members 24 may be provided at positions overlapping the elastic sheet 30, so that a stretchable structure using both elastic members can be provided. In addition, in the illustrated embodiment, the elongated elastic members extending along leg openings are not provided at edge portions of the leg openings in the outer member 20. However, the elongated elastic members may be provided at positions overlapping the elastic sheet 30 at the edge portions or instead of the elastic sheet 30 at the edge portions.

As other embodiments, although not illustrated, appropriate modifications can be made. For example, the elastic sheet stretchable structure 20X may not be provided in the intermediate portion L between the lower torso portion T of the front body F and the lower torso portion T of the back body B, the elastic sheet stretchable structure 20X may be continuously provided in the front-back direction LD from the inside of the lower torso portion T of the front body F to the inside of the lower torso portion T of the back body B via the intermediate portion L, or the elastic sheet stretchable structure 20X may be provided only in one of the front body F and the back body B.

(Stretchable Region)

A region having the elastic sheet stretchable structure 20X in the outer member 20 has a stretchable region that can be stretched and contracted in the width direction WD. The stretchable region 80 contracts in the width direction WD by a contraction force of the elastic sheet 30 and is extensible in the width direction WD. More specifically, in a state where the elastic sheet 30 is stretched in the width direction WD, the first sheet layer 20A and the second sheet layer 20B are bonded through the joint holes 31 of the elastic sheet 30 at intervals in each of the width direction WD and the front-back direction LD orthogonal thereto (the direction LD orthogonal to the stretchable direction) to form a plurality of sheet joined portions 40, thereby forming the elastic sheet stretchable structure 20X. Further, in the stretchable region 80, the elastic sheet 30 is left without disconnection in the width direction WD, and the sheet joined portions 40 are disposed such that the first sheet layer 20A and the second sheet layer 20B contract by the contraction force of the elastic sheet 30 and contraction pleats 25 are formed, thereby imparting such elasticity.

The stretchable region 80 may have a portion 32 in which the elastic sheet 30 is linearly continuous along the width direction WD as in an example illustrated in FIG. 9 and may not have the portion 32 as in an example illustrated in FIG. 11 and an example illustrated in FIG. 15.

An arrangement pattern of the sheet joined portions 40 in the stretchable region 80 is preferably as in the example illustrated in FIG. 9, as in the example illustrated in FIG. 11, and as in the example illustrated in FIG. 15. That is, in these examples, in the stretchable region 80, as non-joint bands 51 and 52 in which a part not having the sheet joined portions 40 is continuous in the unfolded state, a first non-joint band 51 linearly continuous along a first direction 51d intersecting the stretchable direction ED at an acute angle (acute intersecting angle θ1) is repeatedly present at intervals in a direction orthogonal to the first direction 51d. In addition, a plurality of sheet joined portions 40 and joint holes 31 are provided at intervals between adjacent first non-joint bands 51 in the stretchable region 80. Further, characteristically, a unit structure including a plurality of the first non-joint bands 51 having different first widths 51$w$ determined as widths in the direction orthogonal to the first direction 51$d$ is repeatedly present in the direction orthogonal to the first direction 51$d$ in the stretchable region 80.

As described above, when the unit structure including the plurality of the first non-joint bands 51 having different first widths 51$w$ is repeatedly present in the direction orthogonal to the first direction 51$d$ in the stretchable region 80, a similar magnitude change in width is formed in a continuous portion of the elastic sheet 30 inside the first non-joint bands 51. That is, when the width 51$w$ of the first non-joint bands 51 is narrow, the width of the continuous portion of the elastic sheet 30 on the inside is narrowed. Further, when the width 51$w$ of the first non-joint bands 51 is wide, the width of the continuous portion of the elastic sheet 30 on the inside is widened. Further, when there is a change in the first width 51$w$ in the continuous portion of the elastic sheet 30 in the first non-joint bands 51, both the continuous portion of the elastic sheet 30 in first non-joint bands 51 having a wide width and the continuous portion of the elastic sheet 30 in first non-joint bands 51 having a narrow width are visually emphasized. As a result, regardless of whether the stretchable region 80 is in the natural length state (see FIG. 13 and FIG. 17) or in the worn state stretched to some extent, an appearance having beautiful oblique stripe patterns is exhibited.

In the stretchable region, the first sheet layer 20A and the second sheet layer 20B between the sheet joined portions 40 swell in a direction in which they are separated from each other, thereby forming contraction pleats 25 extending in the front-back direction LD in the natural length state as illustrated in FIG. 9 and FIG. 14(*b*). Further, in the worn state of being stretched to some extent in the width direction WD, the contraction pleats 25 are left even though the contraction pleats 25 are extended. For this reason, in a state of being contracted to some extent, a size of the contraction pleats 25 in the first non-joint bands 51 changes according to the first width 51$w$ of the first non-joint bands 51, and thus an oblique stripe pattern appears more clearly due to an influence of the contraction pleats 25. In addition, as in the illustrated embodiment, when the first sheet layer 20A and the second sheet layer 20B are not bonded to the elastic sheet 30 at least in a portion other than between the first sheet layer 20A and the second sheet layer 20B in the sheet joined portions 40, gaps are formed between the joint holes 31 and the sheet joined portions 40 in the elastic sheet 30, as can be seen from FIG. 9(*c*) assuming a worn state and FIG. 9(*a*) assuming an unfolded state of the first sheet layer 20A and the second sheet layer 20B, in these states. Even when the material of the elastic sheet 30 is a non-porous film or sheet, air permeability is imparted by the gaps. In particular, in the case of having the portion 32 in which the elastic sheet 30 is linearly continuous along the width direction WD, the joint holes 31 narrow due to further contraction of the elastic sheet 30 and a gap is hardly formed between the joint holes 31 and the sheet joined portions 40 in the natural length state. When the elastic sheet 30 does not have the linearly continuous portion along the width direction WD, a gap remains between the joint holes 31 and the sheet joined portions 40.

The unit structure described above is not limited by the magnitude of the width 51$w$ as long as the plurality of first non-joint bands 51 having different first widths 51$w$ is included. However, it is preferable that a large first width

51$w$ in the first non-joint bands 51 is 1.2 to 60 times that of a first non-joint band 51 having a closest width 51$w$ and a small first width 51$w$ is 0.01 to 0.8 times that of the first non-joint band 51 having the closest width 51$w$.

In addition, in the unit structure described above, as long as the plurality of first non-joint bands 51 having the different first widths 51$w$ is included, the first widths 51$w$ in all the first non-joint bands 51 may be different from each other, and a first width 51$w$ in some of the plurality of non-joint bands 51 may be different from a first width 51$w$ of one or a plurality of other first non-joint bands 51 as illustrated in the figure.

Even if an oblique stripe pattern along the first direction 51$d$ due to the contraction pleats 25 of the first non-joint bands 51 and the continuous portion of the elastic sheet 30 therein appears in the stretchable region 80, when an oblique stripe pattern along another oblique direction is more strongly visually recognized in the same stretchable region 80, there is concern that the oblique stripe pattern due to the contraction pleats 25 of the first non-joint bands 51 and the continuous portion of the elastic sheet 30 therein becomes inconspicuous. On the other hand, it is preferable that a maximum value of the first widths 51$w$ in the first non-joint bands 51 is a maximum value of widths in a direction orthogonal to a continuous direction in all the common non-joint bands 51 and 52 having different inclination directions since an oblique stripe pattern due to the contraction pleats 25 of the first non-joint bands 51 and the continuous portion of the elastic sheet 30 therein is more strongly visually recognized in the stretchable region 80. In this case, the maximum value of the first widths 51$w$ in the first non-joint bands 51 can be determined as appropriate, and is preferably 1.2 to 60 times that of the first non-joint band 51 having the closest width 51$w$. Incidentally, widths of all the non-joint bands 51 and 52 including the first non-joint bands 51 in the direction orthogonal to the continuous direction are not limited and are preferably within a range of 0.02 to 5 mm in a normal case. Naturally, the widths of the non-joint bands 51 and 52 in the direction orthogonal to the continuous direction are the first width 51$w$ in the first non-joint bands 51, which correspond to the linearly continuous portion. Therefore, the widths are equal widths.

A first interval 51$s$ determined as an interval between the adjacent first non-joint bands 51 in the direction orthogonal to the first direction 51$d$ can be determined as appropriate. Therefore, the first interval 51$s$ may be the same as, wider than, or narrower than the first width 51$w$ of the adjacent first non-joint bands 51. As one preferable example, it is possible to mention a mode in which the maximum value of the first widths 51$w$ of the first non-joint bands 51 is smaller than a maximum value of the first interval 51$s$ in the unit structure. In this way, by forming a wide interval portion in the unit structure, the oblique stripe pattern due to the contraction pleats 25 of the first non-joint bands 51 and the continuous portion of the elastic sheet 30 inside thereof is more strongly visually recognized. In this case, the maximum value of the first widths 51$w$ of the first non-joint bands 51 can be determined as appropriate, and is preferably 0.01 to 9 times the maximum value of the first interval 51$s$. Incidentally, intervals between all the non-joint bands 51 and 52 including the first non-joint bands 51 in the direction orthogonal to the continuous direction are not particularly limited and are preferably within a range of 0.3 to 50 mm in a normal case. Naturally, the intervals between the non-joint bands 51 and 52 in the direction orthogonal to the continuous direction correspond to the first interval 51$s$ in the first non-joint bands 51 and correspond to equal intervals in the continuous direction.

In the stretchable region 80, as non-joint bands 51 and 52, the second non-joint bands 52 linearly continuous along a second direction 52$d$ intersecting the stretchable direction ED at an acute angle (acute angle 62 formed by intersecting) other than the first direction 51$d$ may be repeatedly present at intervals in a direction orthogonal to the second direction 52$d$, or the second non-joint bands 52 may not be present. In one preferable mode having the second non-joint bands 52, the non-joint bands 51 and 52 are formed in an oblique lattice shape in the stretchable region 80, the first non-joint bands 51 are continuous portions in one direction in the non-joint bands 51 and 52 having the oblique lattice shape, and the second non-joint bands 52 are continuous portions in another direction in the non-joint bands 51 and 52 having the oblique lattice shape. In this case, the first direction 51$d$ and the second direction 52$d$ are opposite to each other in terms of inclination with respect to the stretchable direction ED. Incidentally, as in the example illustrated in FIG. 11 and the example illustrated in FIG. 15, even in a mode not having the non-joint bands 51 and 52 continuous in the width direction WD (stretchable direction ED), when each of the acute intersecting angles 61 and 62 between the first and second directions 51$d$ and 52$d$ and the stretchable direction ED is 5 to 45 degrees, particularly 10 to 30 degrees in the unfolded state of the stretchable region 80, elasticity in the stretchable region 80 can be sufficiently ensured.

However, when an oblique stripe pattern along an oblique direction of the second non-joint bands 52 is more strongly visually recognized in the same stretchable region 80, there is concern that the oblique stripe pattern due to the contraction pleats 25 of the first non-joint bands 51 and the continuous portion of the elastic sheet 30 therein becomes inconspicuous. Therefore, in the case where the second non-joint bands 52 is present as in the example illustrated in FIG. 15, it is desirable that all the second widths 52$w$ determined as a width of the second non-joint bands 52 in the direction orthogonal to the second direction are the same, or the sheet joined portions 40 are disposed so that the second non-joint bands 52 are not present. In this way, in the stretchable region 80, the oblique stripe pattern due to the contraction pleats 25 of the first non-joint bands 51 and the continuous portion of the elastic sheet 30 inside thereof is more strongly visually recognized.

It is desirable that a maximum elongation of the stretchable region 80 in the width direction WD is 190% or more (preferably 200 to 220%). The maximum elongation of the stretchable region 80 is substantially determined by the stretch rate of the elastic sheet 30 at the time of manufacture, and the maximum elongation decreases due to factors that inhibit contraction in the width direction WD based thereon. A main factor of such inhibition is a ratio of the length L of the sheet joined portions 40 per unit length in the width direction WD, and the maximum elongation decreases as this ratio increases. In a normal case, since the length L of the sheet joined portions 40 has a correlation with an area ratio of the sheet joined portions 40, the maximum elongation of the stretchable region 80 can be adjusted by the area ratio of the sheet joined portions 40.

As in the example illustrated in FIG. 9, in the case where the elastic sheet 30 has a portion 32 which is linearly continuous along the width direction WD, the stretching stress of the stretchable region 80 can be adjusted mainly by a sum of orthogonal dimensions 32$w$ (equal to intervals 31$d$ of the joint holes) of the portion 32 in which the elastic sheet

30 is linearly continuous along the width direction WD (see FIG. 9($a$)). On the other hand, as in the example illustrated in FIG. 11 and the example illustrated in FIG. 15, in the case where the elastic sheet 30 has not the portion which is linearly continuous along the width direction WD, the stretching stress can be adjusted by an acute intersecting angle between the continuous direction of the non-joint bands 51 and 52 and the stretchable direction ED. In a normal case, it is preferable that each of the acute intersecting angles 61 and 62 between the continuous direction of the non-joint bands 51 and 52 and the stretchable direction ED in the unfolded state is set to be more than 0 degrees and 45 degrees or less, particularly a range of 10 to 30 degrees.

The area ratio of the sheet joined portions 40 and the area of each of the sheet joined portions 40 in the stretchable region 80 can be determined as appropriate and are preferably within the following ranges in a normal case.

Area of each of sheet joined portions 40: 0.14 to 3.5 mm$^2$ (particularly 0.14 to 1.0 mm$^2$)

Area ratio of sheet joined portions 40: 1.8 to 19.1% (particularly 1.8 to 10.6%)

As described above, the maximum elongation and stretching stress of the stretchable region 80 can be adjusted by the area of the sheet joined portions 40. Thus, as illustrated in FIG. 7, a plurality of regions having different area ratios of the sheet joined portions 40 may be provided in the stretchable region 80 to change fitting according to the site. In the embodiment illustrated in FIG. 7, edge portion regions 82 of leg openings correspond to a flexibly stretching and contracting region in which the area ratio of the sheet joined portions 40 is high comparing to other regions, and thus the stretching stress is weak.

A shape of each of the sheet joined portions 40 and the joint holes 31 in the natural length state can be determined as appropriate, and may be set to any shape such as a perfect circle, an ellipse, a polygon such as a triangle, a rectangle (see FIG. 9, FIG. 11, and FIG. 15), or a rhombus (see FIG. 10($b$)), a convex lens shape (see FIG. 10($a$)), a concave lens shape (see FIG. 10($c$)), a star shape, a cloud shape, etc. The dimensions of the individual sheet joined portions are not particularly limited. However, a maximum length 40$y$ (approximately equal to a dimension 31$y$ of the joint holes 31 in the orthogonal direction) is preferably 0.5 to 3.0 mm, particularly preferably 0.7 to 1.1 mm, and a maximum width 40$x$ is preferably 0.1 to 3.0 mm, particularly 0.1 to 1.1 mm in the case of a shape that is long in a direction XD orthogonal to the stretchable direction.

Meanwhile, between adjacent first non-joint bands 51, the sheet joined portions 40 are aligned in the first direction 51$d$. In this case, for example, as illustrated in FIG. 16, it is preferable that all the sheet joined portions 40 have an elongated shape in which an acute intersecting angle 63 between the longitudinal direction and the direction orthogonal to the stretchable direction ED is within 10 degrees and a maximum dimension 40$e$ in the stretchable direction ED is 0.1 to 0.4 mm since it is possible to ensure a larger dimension of the first non-joint bands 51 in the stretchable direction ED and to suppress a decrease in elasticity.

In addition, as in the example illustrated in FIG. 11, when the unit structure includes a plurality of first wide non-joint bands 51 having a maximum first width 51$w$ and a plurality of first narrow non-joint bands 51 having a narrower first width 51$w$ adjacent to each other in the direction orthogonal to the first direction 51$d$, it is preferable that sheet joined portions 40 having an elongated shape in which the acute intersecting angle between the longitudinal direction and the second direction 52$d$ is within 5 degrees and a maximum dimension 40*f* in the direction orthogonal to the longitudinal direction is 0.1 to 0.4 mm are aligned at intervals in the first direction 51*d* between the adjacent first wide non-joint bands 51. In addition, it is preferable that sheet joined portions 40 having an elongated shape in which the acute intersecting angle θ3 between the longitudinal direction and the first direction 51*d* is 45 degrees or more and a maximum dimension 40*g* in the direction orthogonal to the longitudinal direction is 0.1 to 0.4 mm are aligned at intervals in the first direction 51*d* between the adjacent first narrow non-joint bands 51. By such a shape and arrangement of the sheet joined portions 40, the contraction pleats 25 of the first non-joint bands 51 and the continuous portion of the elastic sheet 30 therein are particularly visually emphasized due to the small area of sheet joined portions 40.

One row or a plurality of rows of the sheet joined portions 40 (rows of the non-joint bands 51 and 52 in the continuous direction) may be located between the adjacent non-joint bands 51 and 52. In addition, it is preferable that intervals between the sheet joined portions 40 in a row direction are regular. However, all the intervals may not be constant, and some intervals may be different.

(Non-stretchable Region)

In a region having the elastic sheet stretchable structure 20X in the outer member 20, as illustrated in FIG. 7, a non-stretchable region 70 may be provided at least on one side of the stretchable region 80 in the width direction. The non-stretchable region 70 means that a maximum elongation in the stretchable direction is 120% or less. The maximum elongation of the non-stretchable region 70 is preferably 110% or less, and more preferably 100%. Arrangement of the stretchable region 80 and the non-stretchable region 70 can be determined as appropriate. In the case of the outer member 20 of the underpants-type disposable diaper as in the present example, a portion overlapping the absorbent body 13 is a region not requiring stretching and contraction. Thus, as in the illustrated embodiment, it is preferable to form a part or all of the portion overlapping the absorbent body 13 (it is desirable to include almost the entire inner/outer fixing region 10B) into the non-stretchable region 70. Naturally, the non-stretchable region 70 may be provided from a region overlapping the absorbent body 13 to a region not overlapping the absorbent body 13 away from the region in the width direction WD or the front-back direction LD, and the non-stretchable region 70 may be provided only in the region not overlapping the absorbent body 13.

The shape of each of the sheet joined portions 40 in the non-stretchable region 70 is not particularly limited, and may be appropriately selected from the same shapes as those described in the section of the stretchable region 80.

In addition, the area ratio of the sheet joined portions 40 and the area of each of the sheet joined portions 40 in the non-stretchable region can be determined as appropriate. However, in a normal case, the area ratio and the area are preferably within the following ranges since the non-stretchable region 70 does not become hard due to the small area of each of the sheet joined portions 40 and the low area ratio of the sheet joined portions 40.

Area of each of sheet joined portions 40: 0.10 to 0.75 mm² (particularly 0.10 to 0.35 mm²)

Area ratio of sheet joined portions 40: 4 to 13% (particularly 5 to 10%)

The non-stretchable region 70 can be formed by densely disposing the sheet joined portions 40 so that the first sheet layer and the second sheet layer are prevented from being contracted by the contraction force of the elastic sheet 30 to form pleats. Specific examples of a method for forming the non-stretchable region 70 include those shown in, for example, JP 5980355 B2, JP 5918877 B2, JP 5980367 B2, and JP 6049228 B2.

(Bonding Structure of Sheet Joined Portions)

When the first sheet layer 20A and the second sheet layer 20B are bonded in the sheet joined portions 40 through the joint holes 31 formed in the elastic sheet 30, it is desirable that the first sheet layer 20A and the second sheet layer 20B are not bonded to the elastic sheet 30 except at least between the first sheet layer 20A and the second sheet layer 20B in the sheet joined portions 40.

Bonding means for the first sheet layer 20A and the second sheet layer 20B in the sheet joined portions 40 is not particularly limited. For example, the first sheet layer 20A and the second sheet layer 20B may be bonded to each other in the sheet joined portions 40 using a hotmelt adhesive or using bonding means by material welding such as heat sealing or ultrasonic sealing.

In a case in which the first sheet layer 20A and the second sheet layer 20B are bonded through the joint holes 31 of the elastic sheet 30 in the sheet joined portions 40, as a mode in which the sheet joined portions 40 are formed by material welding, it is possible to adopt any one of a first welding mode in which the first sheet layer 20A and the second sheet layer 20B are bonded only by a molten and solidified material 20*m* of a most part or a part of at least one of the first sheet layer 20A and the second sheet layer 20B in the sheet joined portions 40 (see FIG. 18(*a*)), a second welding mode in which the first sheet layer 20A and the second sheet layer 20B are bonded only by a molten and solidified material 30*m* of all, a most part, or a part of the elastic sheet 30 in the sheet joined portions 40 (see FIG. 18(*b*)), and a third welding mode in which both of these modes are combined (see FIG. 18(*c*)), and the second and third welding modes are preferable.

A particularly preferable mode is that the first sheet layer 20A and the second sheet layer 20B are bonded by the molten and solidified material 20*m* of the part of the first sheet layer 20A and the second sheet layer 20B and the molten and solidified material 30*m* of all or the most part of the elastic sheet 30 in the sheet joined portions 40. Incidentally, in the third welding mode illustrated in FIG. 20(*b*), the molten and solidified material 30*m* of the elastic sheet 30 shown in white is seen between molten and solidified materials 20*m* of fibers of the first sheet layer 20A or the second sheet layer 20B shown in black. On the other hand, in the first welding mode illustrated in FIG. 20(*a*), the molten and solidified material of the elastic sheet 30 is not seen between molten and solidified materials 20*m* of fibers of the first sheet layer 20A or the second sheet layer 20B.

When the first sheet layer 20A and the second sheet layer 20B are bonded using the molten and solidified material 20*m* of the most part or the part of at least one of the first sheet layer 20A and the second sheet layer 20B as an adhesive as in the first adhesive mode or the third adhesive mode, it is preferable that a part of the first sheet layer 20A and the second sheet layer 20B is not melted since the sheet joined portions 40 are not hardened.

Incidentally, when the first sheet layer 20A and the second sheet layer 20B are nonwoven fabrics, a case in which a part of the first sheet layer 20A and the second sheet layer 20B does not melt includes a mode in which cores (including a central part of a single component fiber in addition to a core in a composite fiber) are left for all fibers of the sheet joined portions 40 while a surrounding part thereof (including a part of a surface layer side of the single component fiber in addition to a sheath in the composite fiber) melts, and a mode in which even though some fibers do not melt at all, remaining fibers all melt or even though cores are left, a surrounding part thereof melts.

When the first sheet layer 20A and the second sheet layer 20B are bonded using the molten and solidified material 30m of the elastic sheet 30 as an adhesive as in the second welding mode and the third welding mode, peel strength becomes high. In the second welding mode, under the condition that a melting point of at least one of the first sheet layer 20A and the second sheet layer 20B is higher than a melting point of the elastic sheet 30 and a heating temperature at the time of forming the sheet joined portions 40, the elastic sheet 30 is interposed between the first sheet layer 20A and the second sheet layer 20B, a site corresponding to the sheet joined portions 40 is pressurized and heated, and only the elastic sheet 30 is melted. In this way, manufacturing can be performed.

Meanwhile, in the third welding mode, under the condition that a melting point of at least one of the first sheet layer 20A and the second sheet layer 20B is higher than a melting point of the elastic sheet 30, the elastic sheet 30 is interposed between the first sheet layer 20A and the second sheet layer 20B, a site corresponding to the sheet joined portions 40 is pressurized and heated, and at least one of the first sheet layer 20A and the second sheet layer 20B and the elastic sheet 30 are melted. In this way, manufacturing can be performed.

From such a viewpoint, the melting point of the elastic sheet 30 is preferably about 80 to 145° C., the melting point of the first sheet layer 20A and the second sheet layer 20B is preferably about 85 to 190° C., particularly 150 to 190° C., and a difference between the melting point of the first sheet layer 20A and the second sheet layer 20B and the melting point of the elastic sheet 30 is preferably about 60 to 90° C. In addition, the heating temperature is preferably set to about 100 to 150° C.

In the second welding mode and the third welding mode, when the first sheet layer 20A and the second sheet layer 20B are nonwoven fabrics, the molten and solidified material 30m of the elastic sheet 30 may penetrate between fibers over the entire first sheet layer 20A and second sheet layer 20B in the thickness direction in the sheet joined portions 40 as illustrated in FIG. 19(c). However, in a mode in which the molten and solidified material 30m penetrates between the fibers to the middle in the thickness direction as illustrated in FIG. 19(a), or a mode in which the molten and solidified material 30m hardly penetrates between the fibers of the first sheet layer 20A and the second sheet layer 20B as illustrated in FIG. 19(b), flexibility of the sheet joined portions 40 becomes high.

FIG. 21 illustrates an example of an ultrasonic sealing device suitable for forming the second welding mode and the third welding mode. In this ultrasonic sealing device, when the sheet joined portions 40 are formed, the first sheet layer 20A, the elastic sheet 30, and the second sheet layer 20B are fed between an anvil roll 60 having projections 60a formed in the pattern of the sheet joined portions 40 on an outer surface and an ultrasonic horn 61. At this time, for example, by setting a feeding speed of the upstream elastic sheet 30 by a feed drive roll 63 and a nip roll 62 to be lower than a feeding speed on the downstream side of the anvil roll 60 and the ultrasonic horn 61, the elastic sheet 30 is stretched to a predetermined stretch rate in an MD (machine direction, flow direction) through a path from a nip position by the feed drive roll 63 and the nip roll 62 to a seal position by the anvil roll 60 and the ultrasonic horn 61. The stretch rate of the elastic sheet 30 can be set by selecting a speed difference between the anvil roll 60 and the feed drive roll 63, and can be set to about 300% to 500%, for example. Reference character 62 indicates the nip roll.

The first sheet layer 20A, the elastic sheet 30, and the second sheet layer 20B fed between the anvil roll 60 and the ultrasonic horn 61 are heated by ultrasonic vibration energy of the ultrasonic horn 61 while being pressurized between the projections 60a and the ultrasonic horn 61 in a state of being stacked in this order. By melting only the elastic sheet 30 or melting at least one of the first sheet layer 20A and the second sheet layer 20B and the elastic sheet 30, the joint holes 31 are formed in the elastic sheet 30. At the same time, the first sheet layer 20A and the second sheet layer 20B are bonded through the joint holes 31. Therefore, in this case, by selecting a size, a shape, a separation interval, and an arrangement pattern in a roll length direction and a roll circumferential direction of the projections 60a of the anvil roll 60, it is possible to select an area ratio of the sheet joined portions 40.

A reason why the joint holes 31 are formed may not be clear. However, it is considered that the holes are formed when portions corresponding to the projections 60a of the anvil roll 60 in the elastic sheet 30 are melted and detached from the surroundings. In this instance, a portion between adjacent joint holes 31 aligned in the stretchable direction ED in the elastic sheet 30 is cut from portions on both sides in the stretchable direction by the joint holes 31 as illustrated in FIG. 9(a), FIG. 12, and FIG. 13, and loses support on both sides in a contracting direction. Thus, in a range in which continuity in a direction orthogonal to the contracting direction can be maintained, a center side in the direction LD orthogonal to the stretchable direction ED more contracts until the center side is balanced with a center side in the stretchable direction, and the joint holes 31 enlarge in the stretchable direction ED.

A constituent material of the first sheet layer 20A and the second sheet layer 20B can be used without particular limitation as long as the constituent material is a sheet-like material having translucency and allowing the elastic sheet 30 to be visually recognized. However, it is preferable that the constituent material has air permeability. Therefore, it is preferable to use a nonwoven fabric from these viewpoints and in terms of flexibility. A row material of the nonwoven fabric is not particularly limited. For example, examples thereof may include a polyolefin-based synthetic fiber such as polyethylene or polypropylene, a polyester-based synthetic fiber, a polyamide-based synthetic fiber, etc., a recycled fiber such as rayon or cupra, a natural fiber such as cotton, or a mixed fiber, a composite fiber, etc. in which two or more of these materials are used. Further, the nonwoven fabric may be manufactured by any processing.

As a method of fiber bonding in the nonwoven fabric, it is possible to adopt any one of chemical means such as an adhesive or a solvent, physical means such as heating, or so-called entanglement. For example, it is possible to adopt a spunlace method, a spunbond method, a thermal bond method, a meltblown method, a needle punch method, an air through method, a point bond method, etc. In the case of using a nonwoven fabric, a basis weight is preferably set to about 10 to 25 g/m$^2$. Further, a part or all of the first sheet layer 20A and the second sheet layer 20B may correspond to a pair of layers faced to each other by folding a single material. For example, as in the illustrated embodiment, in the waist end portions 23, a constituent material located on the outside may be used as the second sheet layer 20B, a folded portion 20C folded back to an internal surface side at a waist opening edge thereof may be used as the first sheet layer 20A, and the elastic sheet 30 may be interposed therebetween. Further, in other portions, a constituent material located on the inside may be used as the first sheet layer 20A, a constituent material located on the outside may be used as the second sheet layer 20B, and the elastic sheet 30 may be interposed therebetween. Naturally, the constituent material of the first sheet layer 20A and the constituent material of the second sheet layer 20B may be individually provided over the entire region in the front-back direction LD, and the elastic sheet 30 may be interposed between the constituent material of the first sheet layer 20A and the constituent material of the second sheet layer 20B without folding back the constituent materials.

The elastic sheet 30 is not particularly limited, and may correspond to a stretchable nonwoven fabric in addition to the elastic film as long as the sheet is made of a thermoplastic resin having elasticity. Further, as the elastic sheet 30, in addition to a non-porous sheet, it is possible to use a sheet in which a plurality of holes or slits is formed for ventilation. In particular, it is preferable that the elastic sheet 30 has a tensile strength in the width direction WD (stretchable direction ED, MD) of 8 to 25 N/35 mm, a tensile strength in the front-back direction LD (direction XD orthogonal to the stretchable direction, CD (cross direction)) of 5 to 20 N/35 mm, a tensile elongation in the width direction WD of 450 to 1,050%, and a tensile elongation in the front-back direction LD of 450 to 1,400%. A thickness of the elastic sheet 30 is not particularly limited. However, the thickness is preferably about 20 to 40 μm.

Description of Terms in Specification

The following terms in the specification have the following meanings unless otherwise specified in the specification.

The "front body" and the "back body" refer to portions on the front side and the back side, respectively, with respect to a center of the underpants-type disposable diaper in the front-back direction as a boundary. In addition, the crotch portion refers to a range in the front-back direction including the center of the underpants-type disposable diaper in the front-back direction, and refers to a range of a portion having a narrowing portion in the front-back direction when the absorbent body has the narrowing portion.

The "maximum elongation" refers to a maximum value of an elongation in the stretchable direction ED (in other words, an elongation in the unfolded state in which the first sheet layer and the second sheet layer are unfolded flat without contraction or slack), and represents a length in the unfolded state as a percentage when the natural length is 100%.

The "area ratio" refers to a ratio of a target portion to a unit area, and is represented as a percentage of a value obtained by dividing a total area of target portions (for example, the sheet joined portions 40, the openings of the joint holes 31, and the vent holes) in target regions (for example, the stretchable region 80 and the non-stretchable region 70) by an area of the target regions. In particular, the "area ratio" in a region having the stretchable structure refers to an area ratio in the unfolded state. In a mode in which a plurality of target portions is provided at intervals, it is desirable to obtain the area ratio by setting a size of the target regions to include ten or more target portions.

The "stretch rate" refers to a value when the natural length is 100%.

The "basis weight" is measured as below. A sample or a test piece is pre-dried, and then is left in a test room or a device in a standard state (temperature 23±1° C., relative humidity 50±2% in a test location), and is put in a constant weight state. Pre-drying refers to setting the weight of the sample or the test piece to a constant weight in an environment in which temperature is 100° C. Incidentally, pre-drying is unnecessary for a fiber having an official moisture regain of 0.0%. A sample having dimensions of 100 mm×100 mm is cut off from the test piece in the constant weight state using a sampling template (100 mm×100 mm). A weight of the sample is measured and multiplied by 100 to calculate a weight per square meter, and the weight is set to the basis weight.

The "thickness" of the absorbent body is measured using a thickness measuring instrument of Ozaki Mfg. Co., Ltd. (Peacock, Dial Thickness Gauge Large Type, Model J-B (measurement range 0 to 35 mm) or Model K-4 (measurement range 0 to 50 mm)) by horizontally placing the sample and the thickness measuring device. A "thickness" other than the above thickness is automatically measured under the condition of load: 0.098 N/cm² and pressure area: 2 cm² using an automatic thickness meter (KES-G5 handy compression measurement program).

The "tensile strength" and the "tensile elongation (breaking elongation) refer to values measured by setting an initial chuck interval (distance between marked lines) to 50 mm and a tensile speed to 300 mm/min in accordance with JIS K7127: 1999 "Plastics-Determination of tensile properties-" except that the test piece has a rectangular shape of width 35 mm×length 80 mm. As a tensile testing machine, for example, AUTO-GRAPH AGS-G100N manufactured by SHIMADZU CORPORATION can be used.

The "stretching stress" refers to the tensile stress (N/35 mm) measured when stretching in the elastic region by a tensile test setting an initial chuck interval (distance between marked lines) to 50 mm and a tensile speed to 300 mm/min in accordance with JIS K7127: 1999 "Plastics-Determination of tensile properties-", and a degree of stretching can be appropriately determined depending on the test object. It is preferable that the test piece has a rectangular shape having a width of 35 mm and a length of 80 mm or more. However, when a test piece having a width of 35 mm may not be cut out, the test piece is created to have a width allowing cutting out, and a measured value is set to a value converted to have the width of 35 mm. In addition, even in a case in which the target region is small and sufficient test pieces may not be collected, when the magnitude of stretching stress is compared, even a suitably small test piece can be compared at least as long as test pieces of the same size are used. As a tensile testing machine, for example, AUTOGRAPH AGS-G100N manufactured by SHIMADZU CORPORATION can be used.

The "unfolded state" refers to a flatly unfolded state without contraction or slack.

Dimensions of each portion refer to dimensions in an unfolded state rather than the natural length state unless otherwise stated.

When there is no description about an environmental condition in a test or measurement, it is presumed that the test or measurement is performed in a test room or a device in a standard state (temperature 23±1° C., relative humidity 50±2% in a test location).

INDUSTRIAL APPLICABILITY

As long as a stretchable region to which an elastic sheet stretchable structure can be applied is included, the invention can be used for elastic members in general disposable wearing articles such as various disposable diapers of a tape type, a pad type, etc., a sanitary napkin, a disposable wearing article for swimming or playing in the water, etc. in addition to the underpants-type disposable diaper as in the above example.

REFERENCE SIGNS LIST

10 Inner member
10B Inner/outer fixing region
11 Top sheet
12 Liquid impervious sheet
13 Absorbent body
13N Narrower portion
14 Package sheet
17 Non-absorbent body side portion
20 Outer member
20A First sheet layer
20B Second sheet layer
20C Folded portion
20X Elastic film stretchable structure
21 Side seal portion
23 Waist end portion region
24 Waist portion elastic member
25 Contraction pleats
29 Around-leg line
30 Elastic sheet
31 Joint hole
40 Sheet joined portion
51, 52 Non-joint band
51 First non-joint band
51d First direction
51s First interval
51w First width
52 Second non-joint band
52d Second direction
70 Non-stretchable region
80 Stretchable region
90 Three-dimensional gather
93 Fallen portion
94 Free portion
95 Gather sheet
96 Elastically stretchable gather member
B Back body
ED Stretchable direction
F Front body
L Intermediate portion
LD Front-back direction
T Lower torso portion
WD Width direction

The invention claimed is:

1. An elastic member having an elastic sheet stretchable structure in which an elastic sheet is interposed between a first sheet layer and a second sheet layer and the first sheet layer and the second sheet layer are bonded through joint holes penetrating the elastic sheet or via the elastic sheet at a plurality of sheet joined portions arranged at intervals,
    wherein the first sheet layer and the second sheet layer are
        formed of a material having translucency and the elastic sheet is visually recognizable through the first sheet layer and the second sheet layer, a region having the elastic sheet stretchable structure has a stretchable region that contracts in a stretchable direction by contraction of the elastic sheet and is extensible in the stretchable direction,
    first non-joint bands linearly continuous along a first direction intersecting the stretchable direction at an acute angle are repeatedly present at intervals in a direction orthogonal to the first direction as non-joint bands in which a portion not having the sheet joined portions is continuous in an unfolded state in the stretchable region,
    a plurality of sheet joined portions and joint holes are provided at intervals between adjacent first non-joint bands in the stretchable region,
    a unit structure including a plurality of first non-joint bands having different first widths determined as widths in the direction orthogonal to the first direction is repeatedly present in the direction orthogonal to the first direction in the stretchable region, wherein at least one of the plurality of first non-joint bands has a continuous portion of the elastic sheet linearly continuing along the first direction therein, and wherein at least another one of the plurality of first non-joint bands has only a non-continuous portion of the elastic sheet linearly continuing along the first direction therein and does not have a continuous portion of the elastic sheet linearly continuing along the first direction therein, and the stretchable region does not have a portion in which the elastic sheet is linearly continuous along a width direction.

2. The elastic member according to claim 1, wherein a maximum value of the first widths in the first non-joint bands is a maximum value of widths in a direction orthogonal to a continuous direction in all the non-joint bands.

3. The elastic member according to claim 2, wherein in the unit structure, the maximum value of the first widths in the first non-joint bands is smaller than a maximum value of a first interval determined as an interval in the direction orthogonal to the first direction in the adjacent first non-joint bands.

4. The elastic member according to claim 2,
    wherein in the stretchable region,
    second non-joint bands linearly continuous along a second direction intersecting the stretchable direction at an acute angle other than the first direction is repeatedly present as the non-joint bands at intervals in a direction orthogonal to the second direction and all second widths determined as widths in the direction orthogonal to the second direction in the second non-joint bands are the same, or
    the second non-joint bands are not included.

5. The elastic member according to claim 1, wherein in the unit structure, the maximum value of the first widths in the first non-joint bands is smaller than a maximum value of a first interval determined as an interval in the direction orthogonal to the first direction in the adjacent first non-joint bands.

6. The elastic member according to claim 5,
    wherein in the stretchable region,
    second non-joint bands linearly continuous along a second direction intersecting the stretchable direction at an acute angle other than the first direction is repeatedly present as the non-joint bands at intervals in a direction orthogonal to the second direction and all second widths determined as widths in the direction orthogonal to the second direction in the second non-joint bands are the same, or
    the second non-joint bands are not included.

7. The elastic member according to claim 1,
wherein in the stretchable region,
second non-joint bands linearly continuous along a second direction intersecting the stretchable direction at an acute angle other than the first direction is repeatedly present as the non-joint bands at intervals in a direction orthogonal to the second direction and all second widths determined as widths in the direction orthogonal to the second direction in the second non-joint bands are the same, or
the second non-joint bands are not included.

8. The elastic member according to claim 7,
wherein the non-joint bands are formed in an oblique lattice shape in the stretchable region,
the first non-joint bands correspond to portions continuous in one direction in the non-joint bands having the oblique lattice shape,
the second non-joint bands correspond to portions continuous in another direction in the non-joint bands having the oblique lattice shape,
the first direction and the second direction are opposite to each other in terms of inclination with respect to the stretchable direction, and
each of acute intersecting angles between the first and second directions and the stretchable direction is 5 to 45 degrees in the unfolded state of the stretchable region.

9. The elastic member according to claim 8, wherein all the sheet joined portions in the stretchable region have an elongated shape in which an acute intersecting angle between a longitudinal direction and a direction orthogonal to the stretchable direction is within 10 degrees and a maximum dimension in the stretchable direction is 0.1 to 0.4 mm, and inclined with respect to a direction orthogonal to the stretchable direction.

10. The elastic member according to claim 8,
wherein the unit structure includes a plurality of first wide non-joint bands having a maximum first width and a plurality of first narrow non-joint bands having a narrower first width than the maximum first width adjacent to each other in the direction orthogonal to the first direction,
sheet joined portions having an elongated shape in which an acute intersecting angle between a longitudinal direction and the second direction is within 5 degrees and a dimension in a direction orthogonal to the longitudinal direction is 0.1 to 0.4 mm are aligned at intervals in the first direction between the adjacent first wide non-joint bands, and
sheet joined portions having an elongated shape in which an acute intersecting angle between a longitudinal direction and the first direction is 45 degrees or more and a dimension in a direction orthogonal to the longitudinal direction is 0.1 to 0.4 mm are aligned at intervals in the first direction between the adjacent first narrow non-joint bands.

11. An underpants-type disposable wearing article comprising:

an integrated outer member from a front body to a back body or outer members separately provided for the front body and the back body;
an inner member attached to an intermediate portion of the outer member in a width direction to extend to both front and back sides of a crotch portion;
side seal portions in which both side portions of the outer member in the front body and both side portions of the outer member in the back body are bonded to each other; and
a waist opening and a pair of right and left leg openings,
wherein the outer member in at least one of the front body and the back body is an elastic member having an elastic sheet stretchable structure in which the elastic sheet is interposed between a first sheet layer and a second sheet layer and the first sheet layer and the second sheet layer are bonded through joint holes penetrating the elastic sheet or via the elastic sheet at a plurality of sheet joined portions arranged at intervals,
wherein the first sheet layer and the second sheet layer are formed of a material having translucency and the elastic sheet is visually recognizable through the first sheet layer and the second sheet layer,
a region having the elastic sheet stretchable structure has a stretchable region that contracts in a stretchable direction by contraction of the elastic sheet and is extensible in the stretchable direction,
first non-joint bands linearly continuous along a first direction intersecting the stretchable direction at an acute angle are repeatedly present at intervals in a direction orthogonal to the first direction as non-joint bands in which a portion not having the sheet joined portions is continuous in an unfolded state in the stretchable region,
a plurality of sheet joined portions and joint holes are provided at intervals between adjacent first non-joint bands in the stretchable region,
a unit structure including a plurality of first non-joint bands having different first widths determined as widths in the direction orthogonal to the first direction is repeatedly present in the direction orthogonal to the first direction in the stretchable region, wherein at least one of the plurality of first non-joint bands has a continuous portion of the elastic sheet linearly continuing along the first direction therein, at least another one of the plurality of first non-joint bands has only a non-continuous portion of the elastic sheet linearly continuing along the first direction therein and does not have a continuous portion of the elastic sheet linearly continuing along the first direction therein, and the stretchable region does not have a portion in which the elastic sheet is linearly continuous along the width direction, and wherein the elastic sheet stretchable structure is over a range in the width direction corresponding to a space between the side seal portions at least in a partial range in a front-back direction so that the stretchable direction of the stretchable region thereof corresponds to the width direction.

* * * * *